US010488397B2

(12) United States Patent
Maric et al.

(10) Patent No.: US 10,488,397 B2
(45) Date of Patent: Nov. 26, 2019

(54) METAL OXIDE BASED SENSORS FOR SENSING LOW CONCENTRATION OF SPECIFIC GASES PREPARED BY A FLAME BASED PROCESS

(71) Applicant: University of Connecticut, Farmington, CT (US)

(72) Inventors: Radenka Maric, Andover, CT (US); Rishabh Jain, Hillsboro, OR (US)

(73) Assignee: University of Connecticut, Farmington, CT (US)

( * ) Notice: Subject to any disclaimer, the term of this patent is extended or adjusted under 35 U.S.C. 154(b) by 121 days.

(21) Appl. No.: 15/478,727

(22) Filed: Apr. 4, 2017

(65) Prior Publication Data

US 2017/0284999 A1    Oct. 5, 2017

Related U.S. Application Data

(60) Provisional application No. 62/318,593, filed on Apr. 5, 2016.

(51) Int. Cl.
*G01N 27/02* (2006.01)
*G01N 33/497* (2006.01)
(Continued)

(52) U.S. Cl.
CPC ......... *G01N 33/497* (2013.01); *G01N 27/127* (2013.01); *G01N 33/0037* (2013.01);
(Continued)

(58) Field of Classification Search
CPC .... G01N 33/497; G01N 33/483; G01N 33/48; G01N 27/127; G01N 27/125;
(Continued)

(56) References Cited

U.S. PATENT DOCUMENTS 2,920,001 A    1/1960    Smith
5,338,364 A    8/1994    Kurihara
(Continued)

OTHER PUBLICATIONS

Jain et al, Tuning of WO3 Phase Transformation and Structural Modification by Reactive Spray Deposition Technology, Journal of Nanotechnology and Smart Materials, 2014, 1:1-7. (Year: 2014).*
(Continued)

*Primary Examiner* — Christine T Mui
(74) *Attorney, Agent, or Firm* — McCarter & English, LLP

(57) ABSTRACT

Improved sensor assemblies are provided. More particularly, the present disclosure provides improved and highly advantageous metal oxide based sensor assemblies configured to sense low concentration of specific gases, and related methods of use. The present disclosure provides improved physical forms of metal oxide films (e.g., $WO_x$ films, $CeO_x$ films). The exemplary metal oxide films can be fabricated by a Reactive Spray Deposition Technology (RSDT). The highly advantageous films/materials can be utilized in sensor assemblies to detect simple chemical components of the breath that correlate with human health conditions (e.g., the presence of acetone in diabetic patients). These films/materials demonstrate improved thermal stability under the sensor's operating conditions, as well as improved sensitivity to low concentration of the analyte, selectivity and quick responsiveness.

16 Claims, 25 Drawing Sheets

(51) Int. Cl.
*G01N 33/00* (2006.01)
*G01N 27/12* (2006.01)
*G01N 33/48* (2006.01)

(52) U.S. Cl.
CPC . *G01N 33/0047* (2013.01); *G01N 2033/4975* (2013.01); *Y02A 50/245* (2018.01)

(58) Field of Classification Search
CPC ........ G01N 27/12; G01N 27/04; G01N 27/02; Y02A 50/245; Y02A 50/242; Y02A 50/23; Y02A 50/20; Y02A 50/00
USPC ............................... 436/117; 422/84, 83, 50
See application file for complete search history.

(56) References Cited

U.S. PATENT DOCUMENTS

| | | | |
|---|---|---|---|
| 5,445,325 | A | 8/1995 | White |
| 5,932,293 | A | 8/1999 | Belashchenko |
| 6,601,776 | B1 | 8/2003 | Oljaca et al. |
| 6,728,092 | B2 | 4/2004 | Hunt et al. |
| 8,993,472 | B2 | 3/2015 | Roller et al. |
| 2004/0002221 | A1 | 1/2004 | O'Donnell |
| 2008/0280056 | A1 | 11/2008 | Maric et al. |
| 2009/0246398 | A1 | 10/2009 | Kurahashi |
| 2011/0212386 | A1 | 1/2011 | Roller et al. |
| 2015/0141240 | A1 | 5/2015 | Maric et al. |
| 2015/0346190 | A1* | 12/2015 | Sambandan ............ H01L 29/04 73/23.3 |

OTHER PUBLICATIONS

Bhuiyan et al, Gas Sensing Properties of Metal Doped WO3 Thin Film Sensors Prepared by Pulsed Laser Deposition and DC Sputtering Process, Japanese Journal of Applied Physics, vol. 45, No. 10B, 2006, pp. 8469-8472. (Year: 2006).*
Wang et al, Ferroelectric WO3 Nanoparticles for Acetone Selective Detection, Chem. Mater., 2008, 20, 4794-4796. (Year: 2008).*
Roller, "Low Platinum Electrodes for Proton Exchange Fuel Cells Manufactured by Reactive Spray Deposition," Ph.D. Thesis, available online Feb. 2009.
PCT International Search Report and Written Opinion for PCT/US2013/040533 dated Aug. 19, 2013, 7 pages.
U.S. Appl. No. 14/399,593, filed Nov. 7, 2014, US-2015-0141240-A1.
U.S. Appl. No. 62/318,593, filed Apr. 5, 2016.

* cited by examiner

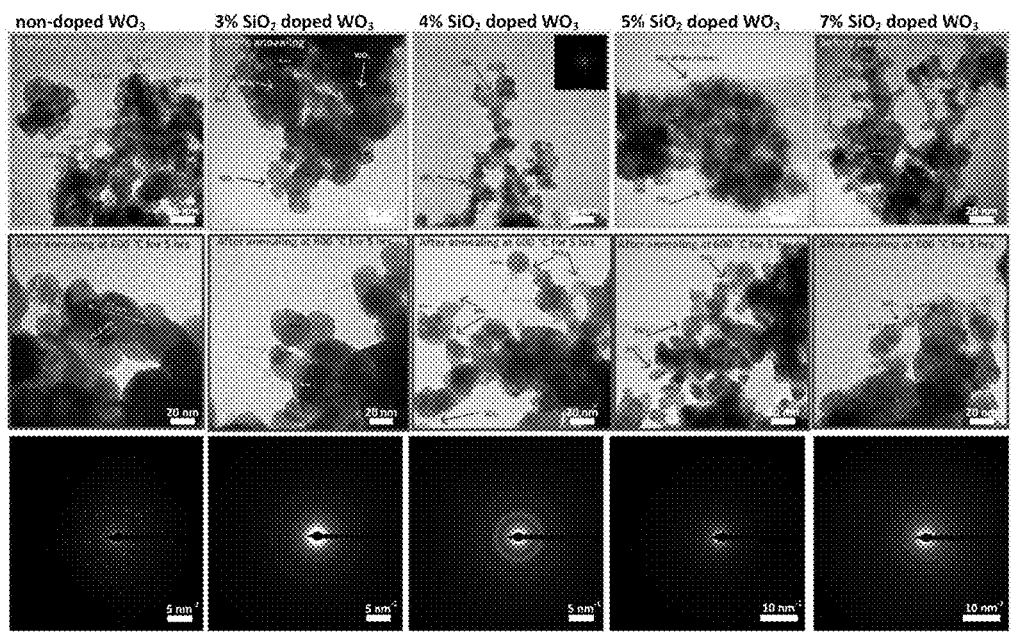

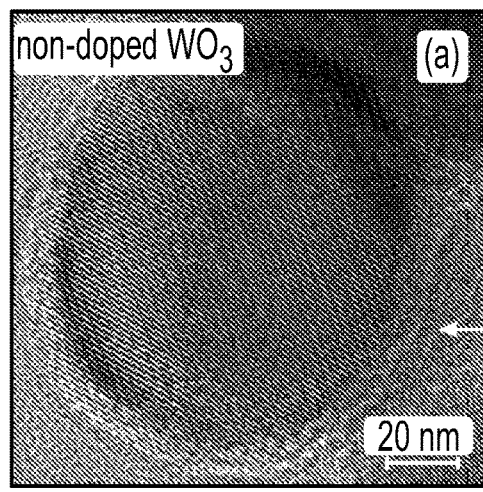
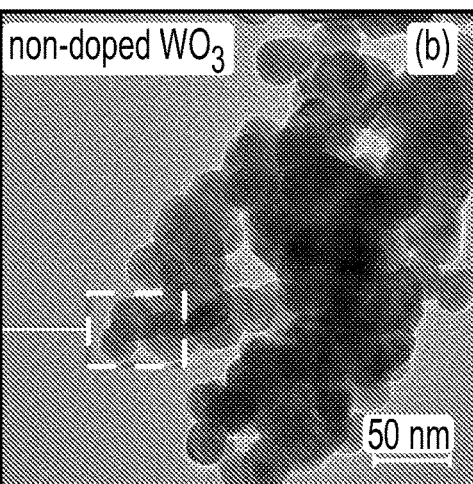
FIG. 2A  FIG. 2B
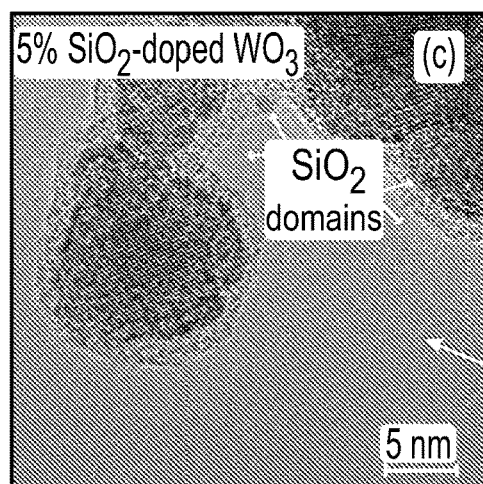
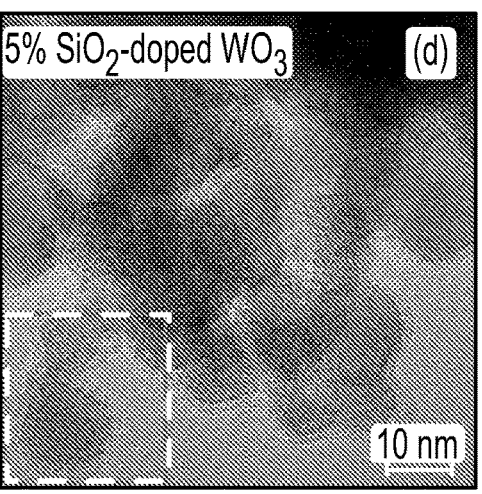
FIG. 2C  FIG. 2D
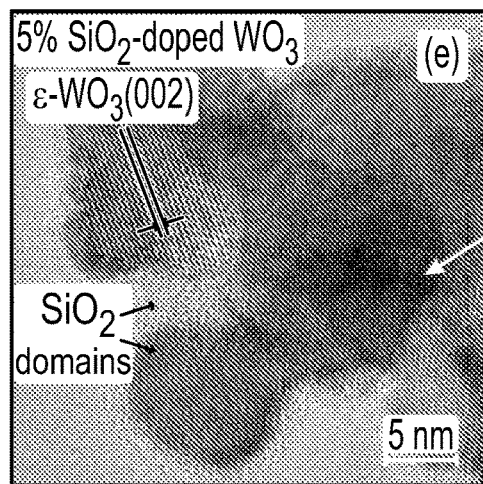
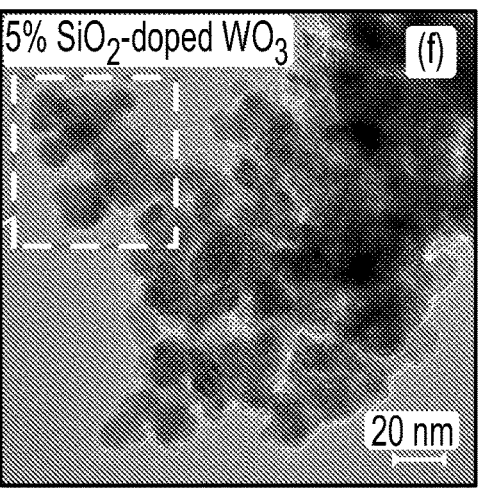
FIG. 2E  FIG. 2F

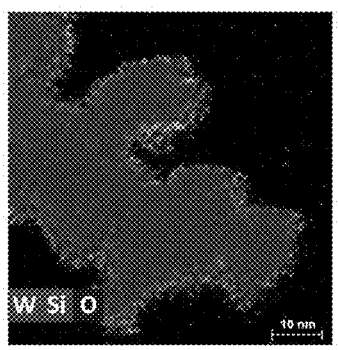
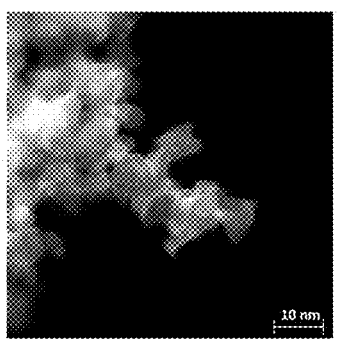
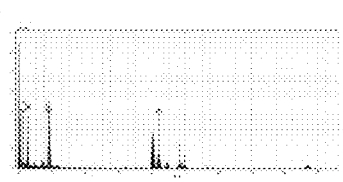
FIG. 3D
FIG. 3E
FIG. 3F

FIG. 12A
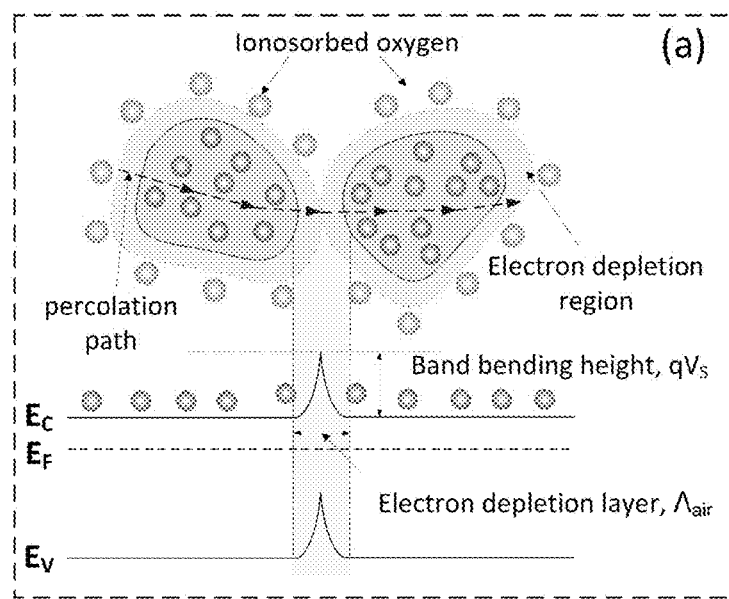
FIG. 12B
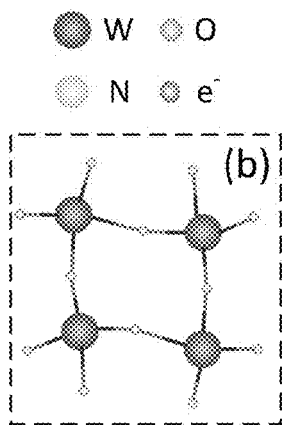
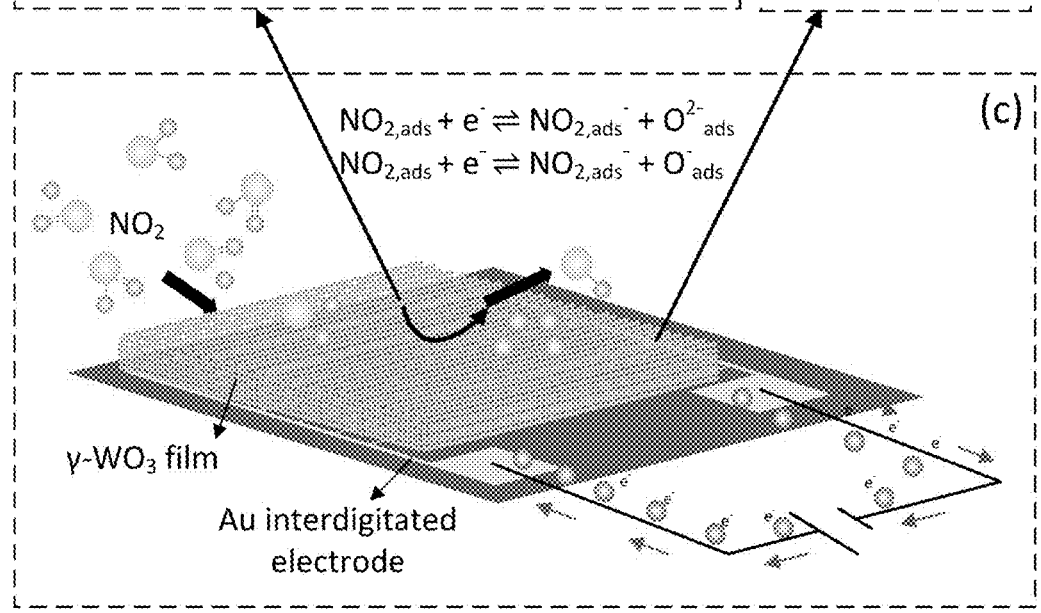
FIG. 12C

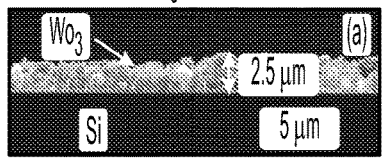
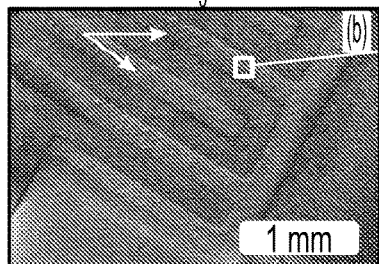
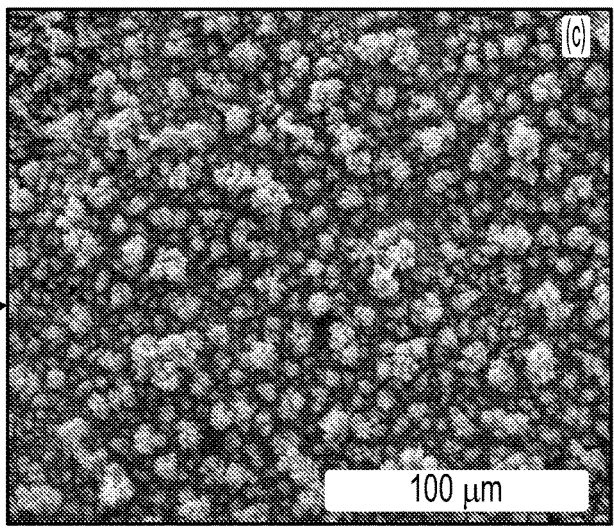
FIG. 16A
FIG. 16B
FIG. 16C
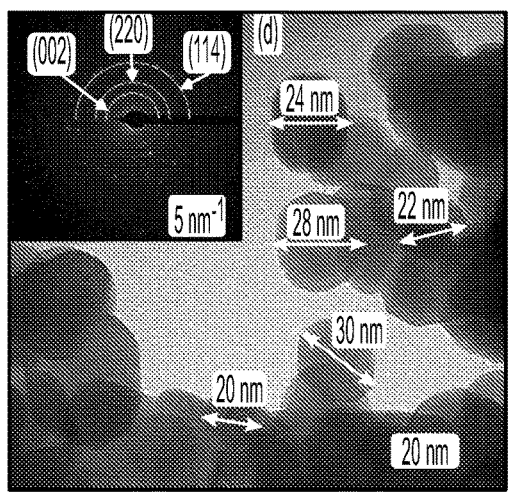
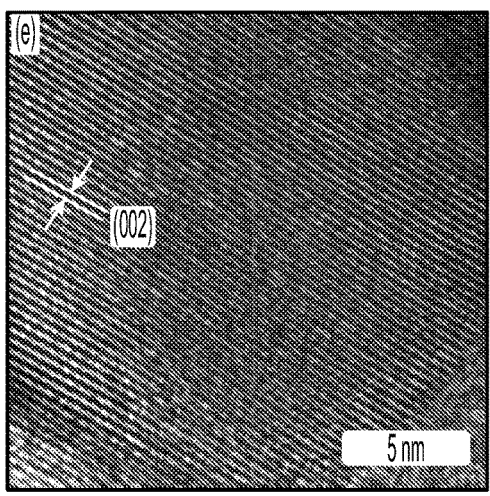
FIG. 16D
FIG. 16E

FIG. 17A
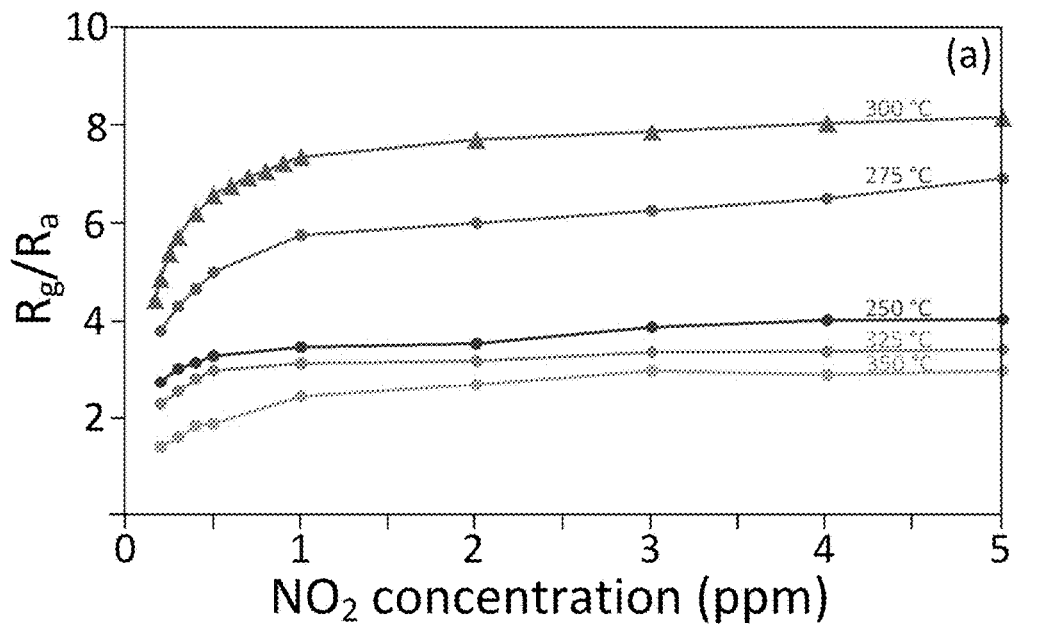
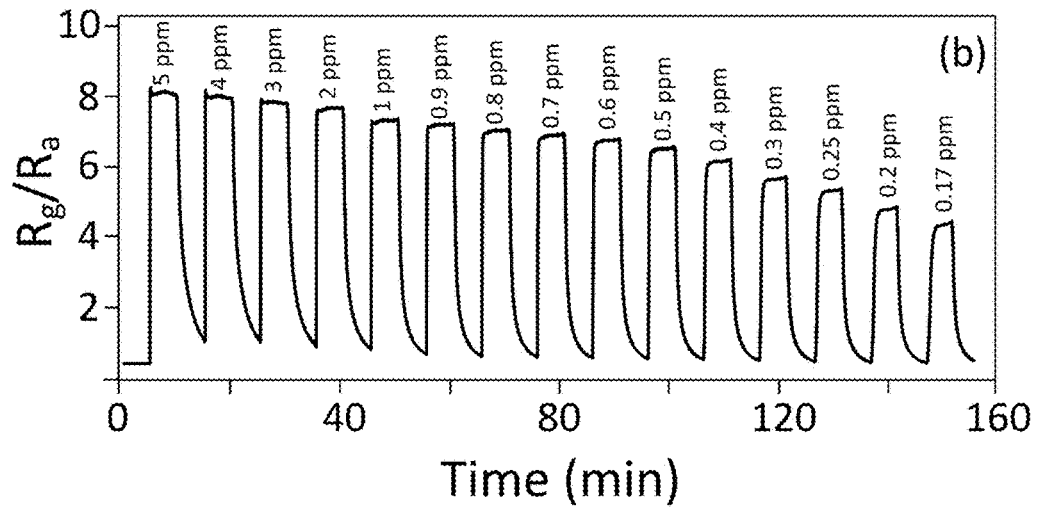
FIG. 17B

FIG. 24A
FIG. 24B
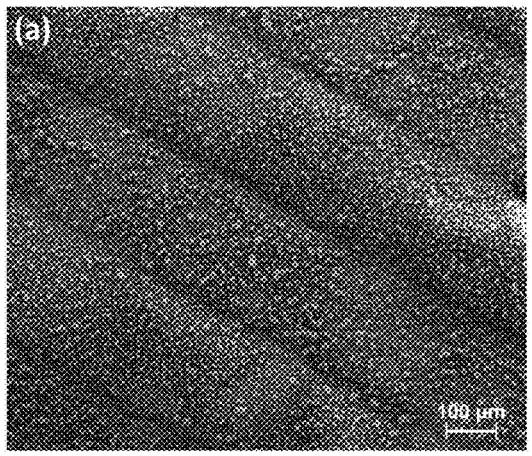
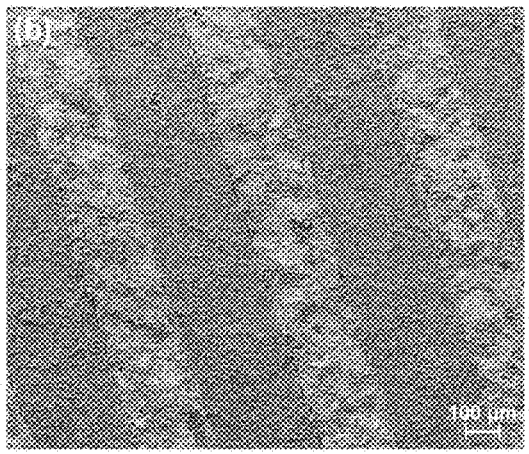
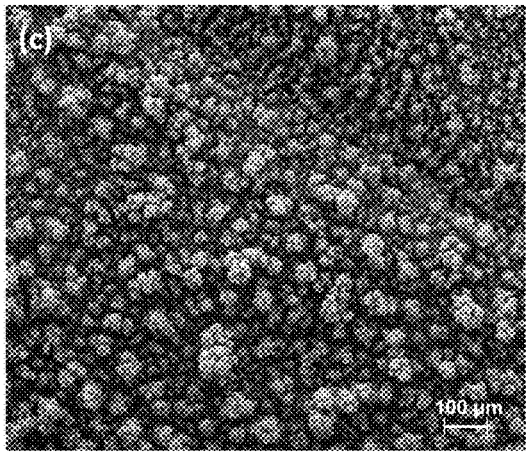
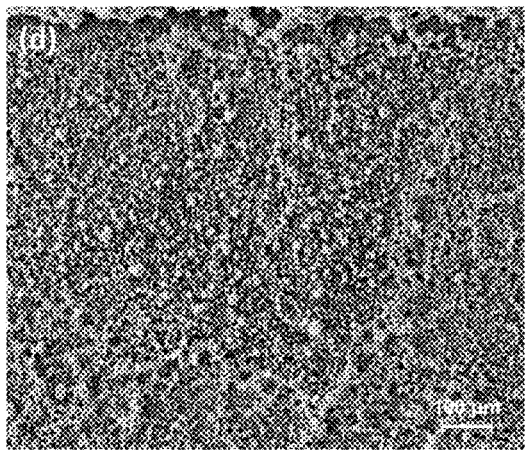
FIG. 24C
FIG. 24D

METAL OXIDE BASED SENSORS FOR SENSING LOW CONCENTRATION OF SPECIFIC GASES PREPARED BY A FLAME BASED PROCESS

CROSS-REFERENCE TO RELATED APPLICATION

The present application claims priority benefit to a provisional patent application entitled "Metal Oxide Based Sensors for Sensing Low Concentration of Specific Gases Prepared by A Flame Based Process," which was filed on Apr. 5, 2016 and assigned Ser. No. 62/318,593. The entire content of the foregoing provisional application is incorporated herein by reference.

RELATED FEDERALLY SPONSORED RESEARCH

This invention was made with government support under Grant No. 1522671 awarded by the U.S. National Science Foundation Innovation Corps. The government has certain rights in the invention.

FIELD OF THE DISCLOSURE

The present disclosure relates to sensor assemblies and, more particularly, to metal oxide based sensor assemblies configured to sense low concentration of specific gases.

BACKGROUND OF THE DISCLOSURE

Presently, evaluation of blood by self-monitoring blood glucose (SMBG) devices is a predominant method for the detection of diabetes. SMBG is recognized by the American Diabetes Association as an important part of effective diabetes self-management. The American Diabetes Association recommends that the patients on multiple-dose insulin or insulin pump therapy should perform SMBG prior to meals and snacks, occasionally postprandially, at bedtime, prior to exercise, when they suspect low blood glucose, after treating low blood glucose until they are normoglycemic, and prior to critical tasks such as driving. This translates to SMBG device use frequency of 6 to 10 times per day.

Current at-home tests (e.g., A1C tests and home pregnancy tests, and monitors for blood glucose, blood pressure and heart rate, and blood cholesterol level) while typically quick, are largely "unconnected" and most are invasive. Only some glucose monitors and breathalyzers provide connections and trending. In addition, at-home tests are typically targeted toward very specific conditions and generally do not enable a broader opportunity for detection and monitoring multiple diseases. In the breath monitoring segment, there are a number of technologies being used, or under development, which do not meet standards necessary for home-based sampling. For example, such technologies can include GC-MS, mini-GC-MS, real-time MS (SIFT, PTR/PTR-ToF, IMS), e-nose, MEMs, diode laser spectroscopy, and mid-IR laser spectroscopy. In general, to be appropriate for home monitoring, a product should have a reasonable cost, be accurate and durable, provide fast real-time results, be portable and allow easy self-administration. Each of the noted technologies has different technical hurdles and/or advantages/disadvantages.

For example, e-nose technology, which recognizes patterns, shows promise but generally has not demonstrated the level of sensitivity and accuracy necessary for pinpointing sub-ppm levels of specific compounds. Several breath tests have received FDA approval, including testing for airway inflammation, $H.\ pylori$, heart transplant rejection, alcohol, and $CO_2$ poisoning. In general, each addresses only one condition and mobile breath sensors manufacturing technologies do not provide desired sensitivity and response times. There are a number of new entrants who are seeking to provide clinical-grade information for the home monitoring market addressing multiple conditions. Focus has typically been on indicators such as blood pressure, pulse, temperature, ECG and blood oxygen levels.

Thus, an interest exists for improved sensor assemblies, and related methods of use. These and other inefficiencies and opportunities for improvement are addressed and/or overcome by the assemblies, systems and methods of the present disclosure.

SUMMARY OF THE DISCLOSURE

The present disclosure provides improved sensor assemblies. More particularly, the present disclosure provides improved metal oxide based sensor assemblies configured to sense low concentration of specific gases.

In exemplary embodiments, the present disclosure provides unique physical forms of metal oxide films (e.g., $WO_x$ films, $CeO_x$ films). The exemplary metal oxide films (e.g., dopant-free metal oxide films) can be fabricated by a Reactive Spray Deposition Technology (RSDT) as described and disclosed in U.S. Patent Pub. No. 2015/0141240, the entire contents of which is hereby incorporated by reference in its entirety. These exemplary films/materials can be utilized in sensor assemblies to detect simple chemical components of the breath that correlate with human health conditions (e.g., the presence of acetone in diabetic patients).

Exemplary reactive spray deposition techniques can enable stabilization of the metal oxide reactive films with unique structural features and high surface areas. These films/materials demonstrate improved thermal stability under the sensor's operating conditions, as well as improved sensitivity to low concentration of the analyte, selectivity and quick responsiveness. In general, the exemplary sensors are low cost sensors.

The present disclosure provides for a sensor assembly including a substrate; a dopant-free metal oxide film deposited on the substrate, the dopant-free metal oxide film having amorphous phase boundaries between particles of the dopant-free metal oxide film; wherein the dopant-free metal oxide film is adapted to facilitate detection of an analyte in a sample.

The present disclosure also provides for a sensor assembly wherein the substrate includes gold or platinum inter-digitated electrodes. The present disclosure also provides for a sensor assembly wherein the substrate is a micro-electro-mechanical-system substrate having a set of inter-digitated electrodes.

The present disclosure also provides for a sensor assembly wherein the dopant-free metal oxide film is porous and has a film thickness of from about 500 nm to about 3 microns. The present disclosure also provides for a sensor assembly wherein the dopant-free metal oxide film includes gamma $WO_3$ or epsilon $WO_3$. The present disclosure also provides for a sensor assembly wherein the dopant-free metal oxide film is selected from the group consisting of a $WO_3$, $TiO_2$, ZnO, $CeO_2$, $WO_x$ and $CeO_x$ film.

The present disclosure also provides for a sensor assembly wherein the dopant-free metal oxide film includes amorphous phase boundaries between nanoparticles of the dopant-free metal oxide film. The present disclosure also provides for a sensor assembly wherein the nanoparticles have a size from about 2 nm to about 30 nm.

The present disclosure also provides for a sensor assembly wherein the dopant-free metal oxide film includes metal oxide phases that are stable at room temperature. The present disclosure also provides for a sensor assembly wherein the dopant-free metal oxide film has uniform necking between particles of the dopant-free metal oxide film.

The present disclosure also provides for a sensor assembly wherein the dopant-free metal oxide film is adapted to facilitate detection of about 0.20 parts per million of the analyte in the sample in less than about 10 seconds. The present disclosure also provides for a sensor assembly wherein the dopant-free metal oxide film is adapted to facilitate detection of the analyte for about 450 hours of continuous testing of the sample at a working temperature of from about 250° C. to about 400° C.

The present disclosure also provides for a sensor assembly wherein the analyte is a gas and the sample includes exhaled breath. The present disclosure also provides for a sensor assembly wherein the analyte is acetone and the sample includes exhaled breath. The present disclosure also provides for a sensor assembly wherein the analyte is $NO_2$ or $NO_x$.

The present disclosure also provides for a sensor assembly wherein the analyte is a component of exhaled breath that correlates with a health condition.

The present disclosure also provides for a sensor assembly wherein the analyte is selected from the group consisting of acetone, $NO_2$, $NO_x$, isoprene, $CO_2$, CO, $O_2$, ethanol and $H_2$.

The present disclosure also provides for a method for utilizing a sensor assembly including a) providing a substrate; b) depositing a dopant-free metal oxide film on the substrate to form a sensing assembly, the dopant-free metal oxide film of the sensing assembly having amorphous phase boundaries between particles of the dopant-free metal oxide film; and c) operating the sensing assembly to detect an analyte in a sample.

The present disclosure also provides for a method for utilizing a sensor assembly wherein the sensing assembly is operated at a working temperature of from about 250° C. to about 400° C. for about 450 hours of continuous testing of the sample to detect the analyte. The present disclosure also provides for a method for utilizing a sensor assembly wherein the sensing assembly is operated to detect about 0.20 parts per million of the analyte in the sample in less than about 10 seconds.

The present disclosure also provides for a sensor assembly including a substrate, the substrate a micro-electro-mechanical-system substrate having a set of gold or platinum inter-digitated electrodes; a dopant-free metal oxide film deposited on the substrate, the dopant-free metal oxide film having amorphous phase boundaries between nanoparticles of the dopant-free metal oxide film, the nanoparticles having a size from about 2 nm to about 30 nm; wherein the dopant-free metal oxide film includes gamma $WO_3$ or epsilon $WO_3$; wherein the dopant-free metal oxide film is porous and has a film thickness of from about 500 nm to about 3 microns; wherein the dopant-free metal oxide film has uniform necking between nanoparticles of the dopant-free metal oxide film; wherein the dopant-free metal oxide film is adapted to facilitate detection of an analyte in a sample; wherein the analyte is a component of exhaled breath that correlates with a health condition; and wherein the dopant-free metal oxide film is adapted to facilitate detection of the analyte for about 450 hours of continuous testing of the sample at a working temperature of from about 250° C. to about 400° C.

Any combination or permutation of embodiments is envisioned. Additional advantageous features, functions and applications of the disclosed assemblies, systems and methods of the present disclosure will be apparent from the description which follows, particularly when read in conjunction with the appended figures. The references, publications and patents listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein:

FIGS. 1A-1E show transmission electron microscopy of the pre annealed and post annealed $WO_3$ film and the corresponding selected area diffraction pattern (SADP);

FIGS. 2A-2F show high resolution transmission electron microscopy of the post annealed $WO_3$ film. (a)-(b) non-doped $WO_3$, (c)-(f) 5 wt % $SiO_2$ doped $WO_3$;

FIGS. 3A-3F show X-ray energy dispersive spectroscopy (XEDS) elemental maps for 5 wt % $SiO_2$ doped $WO_3$ along with the scanning transmission electron microscopy (STEM) image;

FIGS. 12A-12C show a model explaining the $NO_2$ sensing phenomenon by monoclinic γ-$WO_3$; (a) Band bending after ionosorption of oxygen—$E_C$, $E_F$ and $E_V$ denotes the energy of conduction band, Fermi level and valence band respectively; $qV_S$ and $2\Lambda_{gas}$ denotes the band bending height and thickness respectively; (b) Structure of γ-$WO_3$; (c) γ-$WO_3$ thin film deposited on a gold interdigitated electrode;

FIGS. 16A-16C show microscopy images of $WO_3$ deposited by RSDT: (a) Cross-section of the $WO_3$ film on a Si substrate showing a thickness of 2.5 μm, (b) $WO_3$ film deposited on gold interdigitated electrodes, (c) higher magnification view of the $WO_3$ film on a gold line; FIGS. 11D-11E show Transmission electron microscopy (TEM) images of $WO_3$ films deposited by RSDT: (d) $WO_3$ primary particle size in the range 20-30 nm; Selected area diffraction pattern (SADP) is shown in the inset, (e) high resolution image of a $WO_3$ particle showing lattice fringes corresponding to the (002) plane;

FIG. 17A-17B: (a) Relation between sensor response ($R_a$=resistance of $WO_3$ film in pure air, $R_g$=resistance of $WO_3$ film in $NO_2$) and $NO_2$ concentration at different temperatures; (b) $NO_2$ sensing tests conducted at 0.17 to 5 ppm $NO_2$ in the air conducted at 300° C. at 100% r.h. and 1500 sccm flow rate of gases; The tests shown above were conducted on the same sample;

FIGS. 24A-24D show SEM micrographs of the $WO_3$ film before and after the acetone sensing stability test.

DETAILED DESCRIPTION OF THE DISCLOSURE

Figure 3A:
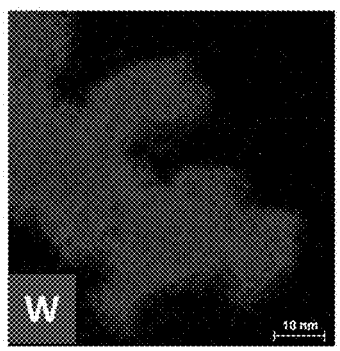
Figure 3B:
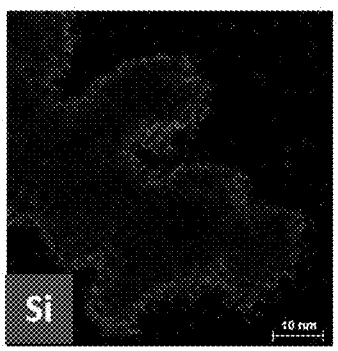
Figure 3C:
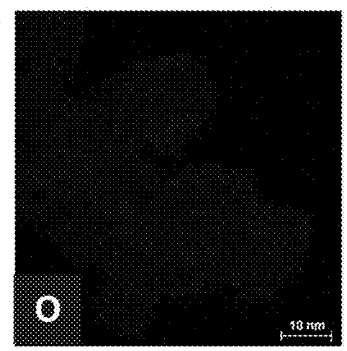

The exemplary embodiments disclosed herein are illustrative of advantageous sensor assemblies (e.g., metal oxide based sensor assemblies configured to sense low concentration of specific gases), and systems of the present disclosure and methods/techniques thereof. It should be understood, however, that the disclosed embodiments are merely exemplary of the present disclosure, which may be embodied in various forms. Therefore, details disclosed herein with reference to exemplary systems/assemblies and associated processes/techniques of assembly and use are not to be interpreted as limiting, but merely as the basis for teaching one skilled in the art how to make and use the advantageous assemblies, systems and methods of the present disclosure.

The present disclosure provides advantageous sensor assemblies. More particularly, the present disclosure provides advantageous metal oxide based sensor assemblies configured to sense low concentration of specific gases, and related methods of use.

In general, the present disclosure provides improved physical forms of metal oxide films (e.g., $WO_x$ films, $CeO_x$ films). The exemplary metal oxide films (e.g., dopant-free metal oxide films) can be fabricated by a Reactive Spray Deposition Technology (RSDT) as described and disclosed in U.S. Patent Pub. No. 2015/0141240. In some embodiments, the highly advantageous films/materials can be utilized in sensor assemblies to detect simple chemical components of the breath that correlate with human health conditions (e.g., the presence of acetone in diabetic patients).

For example, some reactive spray deposition techniques can enable stabilization of the metal oxide reactive films with unique structural features and high surface areas. In general, these films/materials demonstrate improved thermal stability during operating conditions of the sensor, as well as improved sensitivity to low concentration of the analyte, selectivity and quick responsiveness. The exemplary sensors can be low cost sensors.

In exemplary embodiments, the present disclosure provides for gas sensor assemblies using ferroelectric materials such as, without limitation, $WO_3$, $TiO_2$, ZnO, $CeO_2$, etc. The selectivity, response times, and stability of the sensor assemblies can depend on the chemical composition, crystalline phase, and size of the particles. For example, nanomaterials with diameters less than or equal to 10 nm have been observed to provide faster response times and higher selectivity in a ppb range.

One uniqueness is that an exemplary RSDT process can create nanoparticles with controlled size (e.g., 2-20 nm), controlled porosity (e.g., 10% to 40% porosity), and can create thin films with improved mechanical adhesion between the nanoparticles and the substrate electrode and having controlled thickness (e.g., film thicknesses from about 500 nm to about 3 microns).

An exemplary RSDT process can create metastable metal oxide phases that are stable at room temperature (e.g., 18 to 24° C.) by creating amorphous phase boundaries between the grains or particles. It is noted that other technologies stabilize the metastable phase with dopants (e.g., Cr, Si, etc.) that are not required when amorphous boundaries are employed by the exemplary films of the present disclosure.

Sensor arrays can be fabricated to detect several different gas analytes in a sample. The sensors can be fabricated as an array where different arrays can operate at independently controlled temperatures to detect different gas phase components of a gas samples. Exemplary embodiments can be used to monitor the trend of breath in order to diagnose and prevent many conditions (e.g., diabetes, asthma, high cholesterol, etc.).

An exemplary assembly, which includes a metal oxide nanoparticle thin film deposited on a gold inter-digitated electrode, can be fabricated by a flame based process, and can be utilized to measure the contents of human breath (e.g., measure the acetone, NOx, isoprene, $CO_2$, CO, $O_2$ content of human breath).

The market for mobile health innovation can be driven by: (1) the availability and power of mobile computing, (2) a patients' desire for more engagement in their healthcare and for clinical-grade personal health information which is interpreted, (3) health providers need to reduce costs and improve outcomes due to reimbursement changes that reward quality instead of volume, and (4) technical advancements enabling more sophisticated tools. In general, there is greater acceptance of patient generated personal information and growing evidence that home monitoring helps keep patients healthy. The potential market is however moderated by obstacles to integration into traditional healthcare delivery including challenges of data integration and interoperability, impact on workflow and productivity, practice culture, and need for reimbursement.

There is a large opportunity for an assembly/device that can accurately and easily detect and monitor multiple diseases. In general, breath analysis for routine health monitoring is very attractive because it is non-invasive. One proposed project may use engineering approaches to transform care by enabling new strategies for prevention and treatment of chronic disease. Human breath is a complex mixture of $N_2$, $CO_2$, $O_2$, water vapor and traces of about 200 other organics and inorganics which are the product of one or more biological phenomenon occurring in the human body. Deviation of the concentration of these organic and inorganic vapors from their normal value can be caused by a slight change in the chemistry of the human body and can be used as a biomarker for an onset of disease. A few examples of commonly occurring organics and inorganics are provided in Table 1.

Quantifying low concentration of these organics with high selectivity and cross sensitivity with other gases can prove challenging with conventional conductometric sensing capabilities. It is noted that the healthcare sector for diagnostics and patient monitoring using non-invasive breathalyzers is still in its infancy, but has a potential for growth in the coming years.

TABLE 1

Analytes in human breath and the respective disease biomarker

| Compound in human breath | Biomarker |
| --- | --- |
| acetone | diabetes |
| carbonyl sulfide, carbon disulphide, isoprene | liver diseases |
| naphthalene, 1-methyl-, 3-heptanone, methylcyclododecane, etc. | pulmonary tuberculosis |
| nonane, tridecane, 5-methyl, undecane, 3-methyl, etc. | breast cancer |
| benzene, 1,1-oxybis-, 1,1-biphenyl, 2,2-diethyl, furan, 2,5-dimethyl-, etc. | lung cancer |
| ammonia | renal disease |
| octane, 4-methyl, decane, 4-methyl, hexane, etc. | unstable angina |
| propane, 2-methyl, octadecane, octane, 5-methyl, etc. | heart transplant rejection |
| pentane, carbon disulfide | schizophrenia |
| pentane | acute myocardial infarction |
| pentane | acute asthma |
| pentane | rheumatoid arthritis |
| ethane | active ulcerative colitis |
| nitric oxide | asthmatic inflammation |
| nitric oxide | bronchiectasis |
| carbon monoxide | bronchiectasis |
| nitric oxide | COPD |
| ethane, propane, pentane, etc. | cystic fibrosis |

Using advances in nanotechnology and materials science, the present disclosure can provide a multi-sensor array to provide real-time readings of at least four breath markers which indicate diabetes, pulmonary inflammation, liver and kidney malfunction, and blood cholesterol levels. This array can form the core of a breathalyzer that will track breath marker trends, to identify change and signal needed action. An exemplary assembly/device can be fast, non-invasive, mobile, connected, reasonably priced, and easy to use. Conventional mobile breath monitors, as well as development efforts, focus on single diseases. In general, technologies able to read multiple markers do not meet the requirements of self-monitoring.

It is noted that this exemplary technology can be utilized by medical practitioners to measure the breath acetone content of the patients visiting a clinic. As such, the present disclosure provides that a portable device can be fabricated which can be used by the diabetes patients themselves.

In general, there is a large opportunity for an assembly/device that can accurately and easily detect and monitor multiple diseases. Breath analysis for routine health monitoring is very attractive because it typically is non-invasive. Using advances in nanotechnology and materials science, the present disclosure can provide a multi-sensor array to provide real-time readings of at least four breath markers which indicate diabetes, pulmonary inflammation, liver and kidney malfunction, and blood cholesterol levels. This array can form the core of a breathalyzer that will track breath marker trends, to identify change and signal needed action. An exemplary assembly/device may be fast, non-invasive, mobile, connected, reasonably priced, and easy to use. Conventional mobile breath monitors, as well as development efforts, typically focus on single diseases. Conventional technologies able to read multiple markers generally do not meet the requirements of self-monitoring.

Roughly 250 common volatile organic chemicals plus more than 1000 volatile traces, which can indicate specific pathologies, have been identified in exhaled breath. The detection of small differences between healthy and ill people typically requires highly sensitive, selective and durable sensors that can perform in high humidity.

One feature of the assemblies of the present disclosure is that Reactive Spray Deposition Technology (an exemplary sensor manufacturing technology) can provide exceptional sensitivity, selectivity, and durability at a low cost. Some advantages of RSDT result from the ability to use inexpensive, soluble chemical reagents in the open atmosphere without the need for a costly furnace, vacuum, or reaction chamber. As a result, initial system capital and ongoing operating costs are as much as 10 times lower than vacuum-based production methods. The ability to produce thin film directly on an Au electrode in ambient, open-atmosphere conditions can enable continuous production line manufacturing.

By adjusting solution concentrations and constituents, a wide range of compounds can be formed quickly with controlled porosity, nano-particle size and necking, and adhesion to the electrode that can be important for high gas sensitivity. In exemplary embodiments, multiple breath gases have been demonstrated with sensitivities of less than 0.2 parts per million, durability and stability of greater than 300 hours of use (surpassing conventional sensors), response times of less than 10 seconds and having a lack of sensitivity to humidity.

Some currently used technology for measuring blood glucose is difficult and expensive (e.g., because it is invasive and requires patients to prick their fingers to obtain a blood drop which is applied on a plastic test strip connected with a small electronic device). The wounds created after blood glucose testing are prone to infections. Moreover, the presence of other components in the blood (e.g., ascorbic acid, uric acid, acetaminophen, and salicylic acid) can oxidize the $H_2O_2$ thereby falsifying the results. In 2009, the annual cost of test strip supplies for such SMBG devices was reported to be $772 per patient in the United States. Generation of millions of pounds of used test strip as well as the needles used for pricking fingers, possess an additional threat to the environment since they are considered a biohazards and require proper disposal. Improper disposal of used test strips and needles can lead to needle-stick injuries (NSIs) among domestic waste handlers, rag pickers and the community. NSIs could lead to epidemics of blood-borne infections such as HIV/AIDS, hepatitis B and hepatitis C. The lancets used for SMBG are often loosely recapped and are vulnerable to be broken/detached when subjected to minimal force. According to the Centre for Disease Control (Atlanta), outbreaks of hepatitis B have been reported in non-hospital settings due to improper blood glucose monitoring practices. It is also worth noting that there may be a variability in blood sugar levels in finger tips (capillary blood) and forearms (arterial blood) caused by the diffusion of glucose from the plasma to the interstitial fluid as the blood circulates through the capillary system. This might indicate falsely low or high glucose levels.

In exemplary embodiments, the manufacturing RSDT technology can provide both robust technical (faster, more accurate, and more durable sensors) and cost competitive advantages (costs of sensor 10 times lower than current standards). Some advantages of the RSDT process that can be utilized for fabricating exemplary sensor assemblies of the present disclosure are the ability to easily and inexpensively produce different morphologies of materials from the vapor phase in the open atmosphere in a one step process, directly applying film on the Au electrode, with nano-particles size, but without a heat treatment step (e.g., that is needed for many other processes in order to have good adhesion between particles and film and substrate), and providing a good adhesion to the Au electrode. Some differentiators between the exemplary RSDT synthesized sensor assemblies of the present disclosure and conventional sensors synthesized by other techniques for $NO_2$, is a faster response time and higher sensitivity as depicted in Table 2 below. These advantages can be produced by the ability to create a thin film with high adhesion to the electrodes and with nanoparticles which leads to a high sensitivity (e.g., in ppb), high stability (e.g., 300 hours of continuous testing) and fast response (e.g., less than 10 seconds), which are substantial improvements over conventional technologies.

The present disclosure can demonstrate the ability to measure acetone, NOx, isoprene, CO and $CO_2$. In recent findings, including the elimination of $H_2$ cross contamination, the present disclosure can demonstrate the ability to increase acetone sensitivity to a level of less than 0.2 ppm, a much lower level than current state of the art acetone sensors.

The present disclosure can also demonstrate the direct application of ε-$WO_3$ using RSDT. One goal can be to increase the acetone sensitivity compared to state of the art acetone sensors, and demonstrate stability at 400° C.

In this effort, the present disclosure can provide for the direct deposition of ε-$WO_3$ layer (Si doped and un-doped layer) onto Micro-Electro-Mechanical Systems (MEMS) substrates featuring a set of inter-digitated Pt electrodes and a sensing area of 1 $mm^2$ (FIG. 1).

In addition, the exemplary sensor assembly exhibited a response time below 10 seconds (e.g., making these devices attractive for breath analysis), high durability and stability of up to 300 hours (a much longer duration than is demonstrated in with conventional technologies), and a lack of sensitivity to humidity.

One way to discriminate the interference towards these gases is to utilize a sensor with various sensor electrodes to filter out the response from the interfering analytes. Another method is to use filters upstream of the electrode to filter out the gases. Additional technical risks can relate to the design and structure of the array. A possible need for multiple electrodes can be determined and the associated signal process can be developed.

One end product of this research can be an integrated single probe, with multiple sensors, capable of detecting multiple gases so as to be as accurate as possible in diagnosing and monitoring a patient's disease state. A design of the array can be such that it can be extendable to other sensor combinations depending on future applications. The detection of small concentrations of VOC differences in exhaled breath between healthy and ill people can require a gas sensor that fulfills many requirements, notably sensing performance (e.g., sensitivity, selectivity, and rate of response) and reliability (e.g., drift, stability and interfering gases).

Meeting these requirements can be dependent upon the sensing materials used. Therefore that selection and processing of the sensing materials (materials design) can have importance in the research and development of gas sensors. Some operating characteristics of solid-state gas sensors, especially sensitivity, are controlled by at least three independent factors: (1) receptor (recognition) function that provides the ability of the oxide surface to interact with the target gas, (2) transducer function that provides the ability to convert the signal caused by chemical interaction of the oxide surface into electrical signal, and (3) peculiarities of sensor construction. The surface of metal oxides can be responsible for receptor function of solid-state gas sensors. Some key properties, determining a choice of metal oxides, include the following: adsorption ability; electronic, electro-physical and chemical properties; catalytic activity; thermodynamic stability; crystallographic structure; interface state; compatibility with materials and technologies to be used in gas sensors fabrication; reliability, etc.

Some commercially available sensors are currently manufactured with screen printing techniques on small and thin ceramic substrates. However, screen-printed ceramic gas sensors generally need improvement with respect to power consumption, mounting technology and selectivity. In general, the gas sensing property of metal oxide films can depend on the preparation method and the growing conditions of the film itself.

Recently, some thin film synthesis procedures have been proposed. These include spray pyrolysis, drop coating, co-precipitation, sol-gel synthesis, plasma-enhance chemical vapor deposition (PECVD), thermal evaporation, and glancing angle DC magnetron sputtering. Many of these processes are multiple step processes and can require an annealing step. In order to have a high productivity, low resistance, and a low power consumption sensor, some current trends is to construct the sensing elements on a chip by using a thin film technology with a controlled nano-particles size that generally will not have a significant growth and sintering during operation.

Sensing function of a particular analyte can be dependent on the particle size, adhesiveness, porosity, phase, and structure of the metal oxide film. For example, the RSDT process allows the flexibility to create γ-$WO_3$ with control of the particle size, porosity, uniform necking between particles, and thickness of the film. The sensitivity of porous $WO_3$ generally increases when the particle size is below its Debye length (LD) which is 25 nm. This process can employ a broad selection of precursors compared to conventional vapor-fed flame reactors.

In RSDT, nanoparticles are generated in the flame, and then directly deposited on the substrate as a film. This can eliminate the intermediate steps of filtration, drying, and calcination. RSDT can provide complete control of the nanoparticle size, crystallinity, porosity, and film thickness. When developing nano-crystalline thin films, some important requirements are dimensions and morphology control, uniformity, and crystalline properties. In order to obtain one dimensional structures, the growth should have a preferential orientation with a faster growth rate. Utilizing advances in RSDT, exemplary embodiments of the present discourse can provide highly sensitive, selective and durable sensors for use in breath analysis. Metal oxide semiconductors such can converge the electron depletion layer (2Λgas) and the electrical conduction can be dominated by the presence of adsorbed $NO_2$—. Λgas depends on the Debye length (LD) of the material which is 25 nm for $WO_3$.

The RSDT process can allow precise control of the nano-particles size and therefore can allow a much faster response at a low concentration of gas than other technologies presented in Table 2.

TABLE 2

Comparison of γ-$WO_3$ based $NO_2$ sensors prepared by different techniques:

| Synthesis method | Limit of detection (ppm) | Working temperature (° C.) | Response converted to Rg/Ra | Response (used formula) | Response time |
|---|---|---|---|---|---|
| RSDT | 0.17 to 5 | 300 | 4.44 (0.17 ppm)<br>6.58 (0.5 ppm)<br>7.37 (1 ppm)<br>8.07 (5 ppm) | Rg/Ra | 7.2 s |
| Sol-gel ($WO_3$ on porous silicon) | 0.05 to 2 | 25 | Ra/Rg:<br>1.15 (0.05 ppm)<br>1.75 (0.5 ppm)<br>2.01 (1 ppm)<br>3.37 (2 ppm) | Ra/Rg | 2 min |
| Sol-gel ($WO_3$ on alumina) | 0.05 to 2 | 150 | 1.65 (0.5 ppm)<br>2 (1 ppm)<br>2.67 (2 ppm) | Rg/Ra | 2 min |
| DC magnetron sputtering (Porous $WO_3$) | 0.1 to 5 | 150 | 42.2 (1 ppm) | (Rg − Ra)/Ra | 2 min |
| DC magnetron sputtering (Sputtered $WO_3$) | 0.1 to 5 | 200 | 8.2 (1 ppm) | (Rg − Ra)/Ra | 2 min |
| Evaporation condensation | 1 to 200 | 250 | 2 (1 ppm) | (Rg − Ra)/Ra | 70 min |
| Drop coating | 0.5 to 5 | 100 and 200 | 19.2 (1 ppm) | Rg/Ra | 15 min |
| Glancing angle DC magnetron sputtering | 0.1 to 2 | 250 | 4.4 (0.5 ppm) | Rg/Ra | 15 min |
| Induction-heating oxidation of tungsten | 1 to 8 | 110 | 5.5 (1 ppm) | Rg/Ra | 10 min |
| PECVD | 10 to 100 | 200 | 45 (10 ppm) | Vg/Va (same as Rg/Ra) | 50 s |
| Spray pyrolysis | 10 to 100 | 200 | 1.5 (20 ppm) | [(Rg − Ra)/Ra]*100 | 3 s | as n-type $WO_3$ can have remarkable sensing properties for analytes such as, for example, NOx, $NH_3$, acetone, ethanol, and $H_2$.

A comparison between exemplary RSDT synthesized sensors and the sensors synthesized by other techniques for $NO_2$ is shown in Table 2.

It is noted that since the sensing is an adsorption-desorption process, gas diffusion through the film plays a role in the sensor performance. The sensing film should be porous to effectively allow the diffusion process and extend the reaction between $NO_2$ and oxygen from the surface to the bulk.

By assuming steady state conditions, it can be interpreted that the $NO_2$ concentration decreases with the film depth, which can cause the formation of various degrees of reactions at different depths of the film. The resistance change data recorded by the electrochemical analyzer averages the resistances by providing the overall resistance change of the film. Film porosity, thickness, microstructure, and the electrode pattern can be factors which govern this variation. Gas sensing response can be dependent on the particle size of the sensing film. Smaller particles and increased surface area (higher surface to volume ratio) provides a larger number of sites for the surface reaction to occur. At the same time, reducing the particle radius below space-charge layer, Λgas, FIGS. 1A-1E show the bright field TEM micrographs and the SADP of the non-doped and $SiO_2$ doped $WO_3$, both pre annealing and post annealing (600° C.).

The samples were polycrystalline, as evident from the SADP and were indexed to monoclinic $WO_3$. Grain size was measured by TEM point analysis. The initial grain size was in the range of 10 to 15 nm for non-doped doped $WO_3$, 7 to 16 nm for 3 wt % $SiO_2$ doped $WO_3$, 7 to 16 nm for 4 wt % $SiO_2$ doped $WO_3$, 7 to 13 nm for 5 wt % $SiO_2$ doped $WO_3$, 5 to 13 nm for 7 wt % $SiO_2$ doped $WO_3$, and 10 to 15 nm for non-doped doped $WO_3$.

The grain size for the post annealed samples was in the range of 30 to 50 nm for the non-doped $WO_3$, 15 to 35 nm for 3 wt % $SiO_2$ doped $WO_3$, 10 to 20 nm for 4 wt % $SiO_2$ doped $WO_3$, 7 to 17 nm for 5 wt % $SiO_2$ doped $WO_3$, and 10 to 20 nm for 7 wt % $SiO_2$ doped $WO_3$.

Different shapes and sizes of particles were seen from the images. None of the samples shows necking, a property which is desirable for the sensing applications.

FIGS. 2A-2F show the high resolution TEM images of the post annealed (600° C.) $WO_3$.

FIGS. 2A-2B show the non-doped $WO_3$ while FIGS. 2C-2F show the 5 wt % $SiO_2$ doped $WO_3$. Amorphous domains can be clearly seen around the individual grains. It is interesting to observe the amorphous domains in the non-doped $WO_3$. This could be due to the presence of amorphous $WO_3$ which did not crystallize even after the post annealing process. Lattice fringes can be clearly seen in the $WO_3$ grains.

FIGS. 3A-3F show the XEDS elemental map for the 5 wt % $SiO_2$ doped $WO_3$ proving that the amorphous domains in the doped $WO_3$ are $SiO_2$.

This work was performed with a motivation to preserve the metastable ε-$WO_3$ over an extended temperature range desirable for acetone sensors. ε-$WO_3$ phase is polar and preferentially attracts acetone molecules. It was found that the 5 wt % $SiO_2$ doped $WO_3$ performed best in this class with the formation of ε-$WO_3$ in the temperature range 30 to 600° C.

It was determined that the particular structure and properties of $WO_3$ are a function of the synthesis process and doping concentration. However, in spite of obtaining the $WO_3$ phase favorable towards acetone sensing, there was substantially no acetone sensitivity. This could be caused due to the absence of necking between the individual $WO_3$ grains and also due to the possibility that the active sites were blocked by amorphous $SiO_2$ domains.

Figure 4:
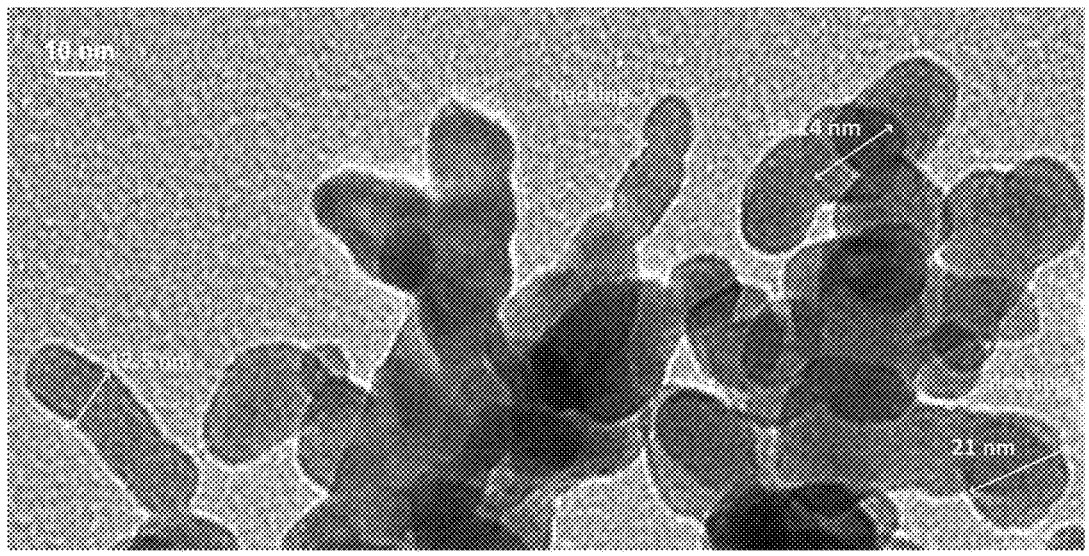
FIG. 4 shows a TEM micrograph of the ε-$WO_3$ crystallites showing necking and a crystallite size (dTEM) distribution ranging between 12-25 nm.

Non-Doped ε-$WO_3$ with Amorphous Domains and Necking:

FIG. 4 shows the bright field TEM micrograph of the non-doped ε-$WO_3$ particles. Necking of the grains can be clearly observed which is advantageous for the enhanced electron transport through the percolation path (grain to grain contact). Various oval shaped particles can be seen.

From a TEM point analysis, a crystallite size (dTEM) distribution ranging between 12 to 25 nm was observed. It has been shown by researchers that the gas sensitivity is significantly enhanced when the crystallite size is smaller than the Debye length ($\lambda D$). This is because both the surface and bulk of the grain contributes to the resistance and yields the largest gas sensor response. The Debye length for $WO_3$ is 25 nm. No evidence of sintering of the nanoparticles was found which is attributed to the use of air quench in RSDT. This sample was highly effective in acetone detection (0.17 to 5 ppm in air).

Figure 5:
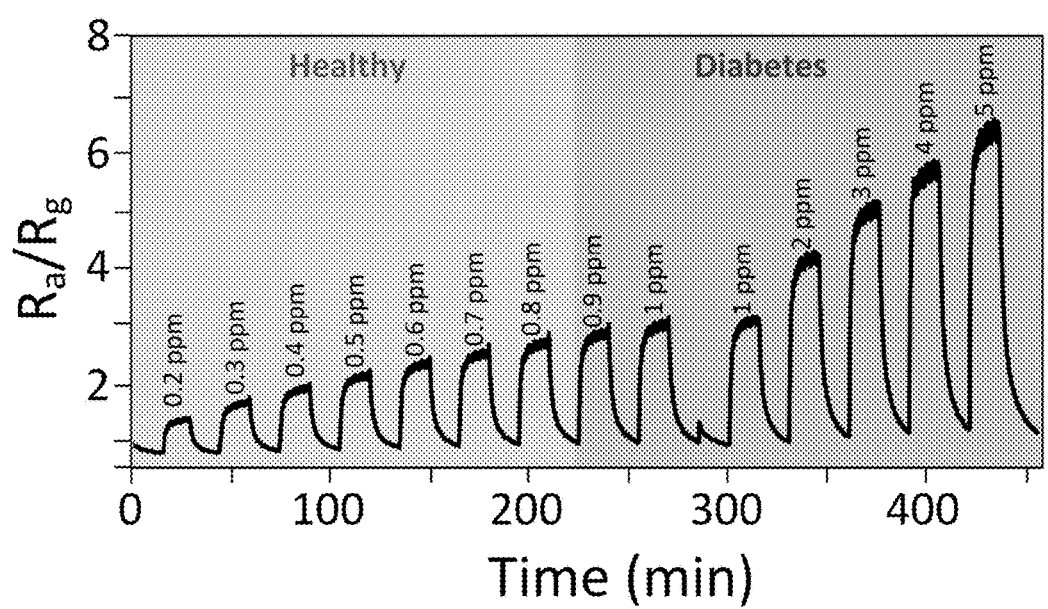
FIG. 5 shows the resistance versus time curve for acetone tests conducted at 400° C. from 0.2 to 1 ppm acetone.

FIG. 5 shows the resistance versus time curve for the acetone concentration ranging from 0.2 to 1 ppm in the air at 400° C. The limit of detection for the tests was 0.2 ppm. The film resistance decreases as the concentration of acetone is increased. This is because of the increased adsorption of acetone molecules at higher acetone concentration. The adsorption and desorption of the acetone molecules on the $WO_3$ film takes place simultaneously and is a reversible process. During the response stage, adsorption is higher than desorption and the resistance of the film increases. This is because acetone diffuses through the porous $WO_3$ film and reduces the $WO_3$ surface thereby depleting the ionosorbed oxygen concentration on the film. Acetone also captures electrons from the conduction band of $WO_3$ causing the formation of an electron depletion region, triggering an increase in its resistance.

It was seen that the sensor response was spontaneous as the gas concentration in the test chamber was changed from pure air to acetone in the air. The response time was calculated to be 10 s. The sensor very quickly stabilized at the maximum value of resistance. At this point, the adsorption rate is equal to the desorption rate. Maximum adsorption had taken place at that particular analyte concentration, and the $WO_3$ film was in equilibrium with the acetone molecules. Recovery of the sensor started when pure air was switched back to the test chamber.

At this point, adsorption was nil and desorption was the only process which was taking place. Presence of two vents in the test chamber expedited the exchange of the gas atmosphere. However it was seen that desorption was still slower than adsorption. A drift can be seen when the resistance of the film is measured in air after exposure to acetone at different concentrations. This is caused by incomplete recovery during the 15 minutes of recovery phase.

Stability Tests:

Stability tests of the $WO_3$ films were conducted for 450 hours at 0.5 ppm acetone in the air at 400° C., and which is substantially the same as the breath acetone concentration of a healthy individual. The sensor was tested at this concentration because it is desirable that the breath acetone concentration remain below the diabetes threshold limit. 0.5 ppm acetone was switched on every 5 minutes (response) followed by 5 minutes of pure air (recovery).

Resistance of the film was measured every 100 ms to record the response and recovery cycle (response+recovery time=10 min).

Figure 6:
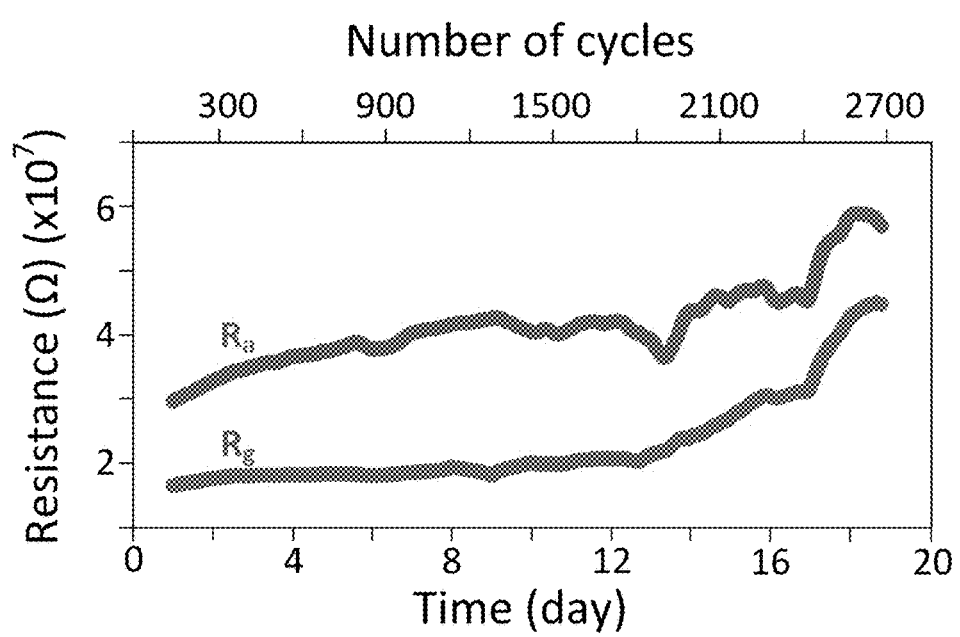
FIG. 6 shows stability tests for a $WO_3$ sensor conducted for 450 hours at 0.5 ppm acetone in the air at 400° C.
Figure 7:
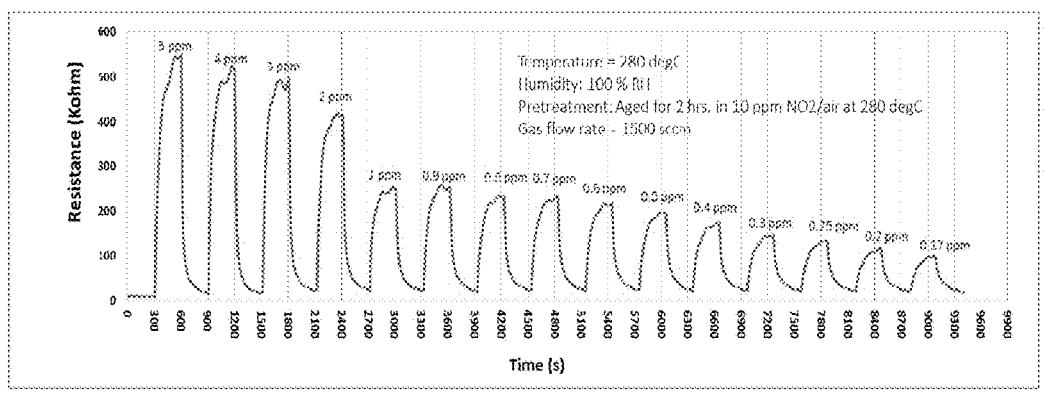
FIG. 7 shows a resistance versus time curve for $NO_2$ tests conducted at 280° C. from 0.17 to 5 ppm $NO_2$ on undoped ZnO nanorods.
Figure 8:
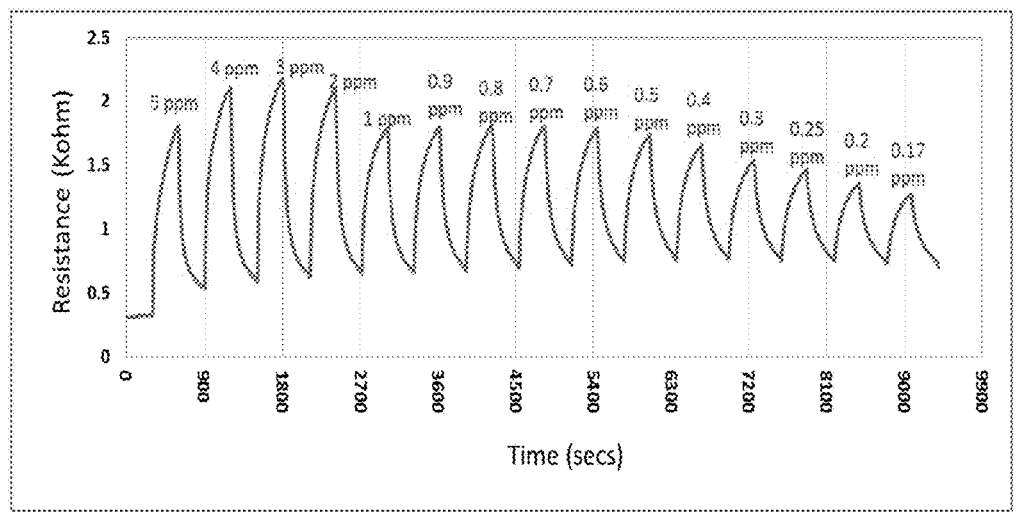
FIG. 8 shows a resistance versus time curve for $NO_2$ tests conducted at 280° C. from 0.17 to 5 ppm $NO_2$ on 5% Ag doped ZnO nanorods.
Figure 9:
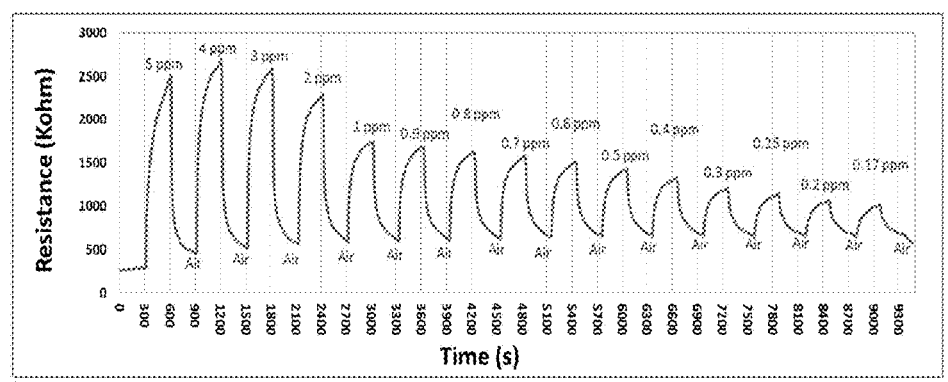
FIG. 9 shows a resistance versus time curve for $NO_2$ tests conducted at 280° C. from 0.17 to 5 ppm $NO_2$ on $CeO_2$ doped ZnO nanorods.
Figure 10:
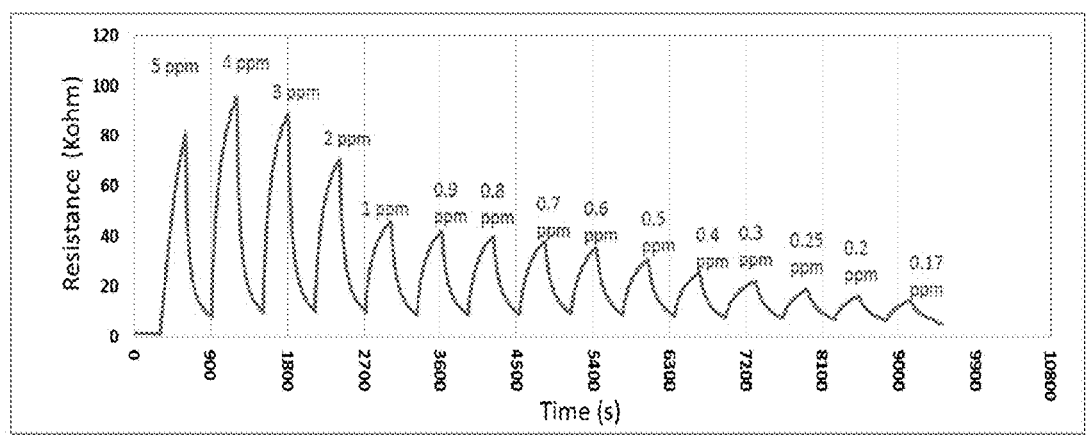
FIG. 10 shows a resistance versus time curve for $NO_2$ tests conducted at 280° C. from 0.17 to 5 ppm $NO_2$ on Mg doped ZnO nanorods.
Figure 11:
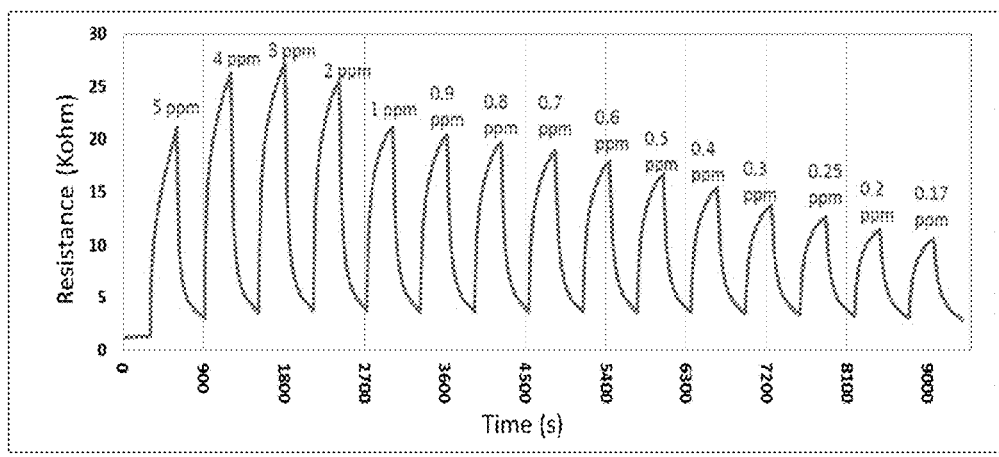
FIG. 11 shows a resistance versus time curve for $NO_2$ tests conducted at 280° C. from 0.17 to 5 ppm $NO_2$ on $TiO_2$ doped ZnO nanorods.

A total of 2700 response-recovery cycles were recorded. FIG. 6 shows the resistance over time for $WO_3$ film in pure air (Ra) and 0.5 ppm acetone in air (Rg), respectively.

It can be seen that the sensor is stable till day 10 (around 250 hours). From day 10 to 21 (250 to 450 hours), the sensor began to degrade possibly due to the growth of the $WO_3$ nanoparticles and the phase transformation to the γ phase as confirmed by XRD and Raman spectroscopy. This shows that maximum degradation of the sensor occurred after day 10 (around 250 hours) as evident from the fluctuation of resistance.

Selectivity:

The response of 0.5 ppm acetone was compared with 10 ppm $H_2$, 0.2 ppm ethanol, 8 ppm CO and 90% relative humidity in air at 400° C. It was seen that the sensor had negligible response for ethanol, CO and humidity, but significant response for 10 ppm $H_2$. It is noted that $H_2$ is a major component exhaled from the human breath. Typical values of $H_2$ in the breath range from 10 to 20 ppm.

TABLE 3

Comparison of the metal oxide based acetone sensors prepared by different synthesis techniques:

| Sensing film | Synthesis method | Limit of detection (LOD) (ppm) | Working temp. (° C.) | Sensitivity ($R_a/R_g$) | Sensitivity (used formula) | Response time (sec) |
|---|---|---|---|---|---|---|
| Pure $WO_3$ | RSDT | 0.2 | 400 | 1.3 (0.2 ppm) 2.1 (0.5 ppm) | $R_a/R_g$ | 10 |
| $Cr_2O_3$—$WO_3$ | Flame spray pyrolysis | 0.2 | 400 | 1.5 (0.2 ppm) | $R_a/R_g$ | 333 |

TABLE 3-continued

Comparison of the metal oxide based acetone sensors prepared by different synthesis techniques:

| Sensing film | Synthesis method | Limit of detection (LOD) (ppm) | Working temp. (° C.) | Sensitivity ($R_a/R_g$) | Sensitivity (used formula) | Response time (sec) |
|---|---|---|---|---|---|---|
| 5 mol % $Cr_2O_3$—$WO_3$ | Sol-gel | 0.5 | 320 | 1.2 (0.5 ppm) | $R_a/R_g$ | 182 |
| $Si_2O_3$—$WO_3$ | Flame spray pyrolysis | 0.02 | 400 | 1.3 (0.02 ppm) 5.2 (0.5 ppm) | $(R_a/R_g)$-1 | 172 |
| Pure $SnO_2$ | Dip-coating | 2 | room temp. | 4 (2 ppm) | $R_a/R_g$ | 30 s |
| Ce—$SnO_2$ | Sol-gel and dip coating | 100 | 210 | 79 (100 ppm) | $R_a/R_g$ | not mentioned |
| $SnO_2$—ZnO | Wet method | 200 | 300 | 2.3 (200 ppm) | $R_a/R_g$ | 233 |
| ZnO | RF reactive sputtering | 15 | 400 | 1.006 (15 ppm) | $(R_a/R_g)$-1 | 324 |
| $TiO_2$ | Flame spray pyrolysis | 1 | 500 | 4 (1 ppm) | $(R_a/R_g)$-1 | 3 |

In the present disclosure, it is noted that exemplary sensor assemblies advantageously utilize a substantially pure $WO_3$ film without the need for dopants (e.g., they utilize a dopant-free $WO_3$ film).

In RSDT, many processes (e.g., combustion, annealing, drop coating on sensors, etc.) are performed in a single step thereby significantly reducing the time and wastage of solvents. In RSDT, nano-particles are generated in the flame, and then are either directly deposited on the substrate as a film or collected as a nanopowder. This eliminates the intermediate steps of filtration, drying, and calcination. RSDT provides complete control of the nanoparticle size, crystallinity, porosity, film thickness, and support concentration.

The present disclosure will be further described with respect to the following examples; however, the scope of the disclosure is not limited thereby. The following examples illustrate, inter alia, the advantageous sensor assemblies (e.g., metal oxide based sensor assemblies configured to sense low concentration of specific gases), and related methods of use.

Example 1:—Ultra-Low $NO_2$ Detection by Gamma $WO_3$ Synthesized by Reactive Spray Deposition Technology A porous tungsten oxide ($WO_3$) $NO_2$ sensor was developed by a one-step flame based process called Reactive Spray Deposition Technology (RSDT). This nano-crystalline $WO_3$ film was deposited directly on gold interdigitated electrodes. The sensitivity of this $NO_2$ sensor was measured at the parts per million (ppm) level, (0.175 ppm in air) at 300° C. and 100% relative humidity. The sensors showed a relatively fast response time (around 7 seconds) and recovery time (around 5 min), respectively. The stability of the sensor was evaluated for 300 hours in 0.5 ppm $NO_2$ in air at 100% relative humidity (2000 response-recovery cycles). The sensor was stable up to 6 days (around 150 h) of continuous operation and degraded between 150 to 300 h. The morphology and surface properties of the $WO_3$ film were investigated with XRD, Raman spectroscopy, BET, SEM, TEM, and HRTEM.

$NO_x$ ($NO_2$, NO) is a toxic air pollutant which is produced as a byproduct of gasoline combustion in an internal combustion engine. Exposure to unsafe levels of $NO_2$ (greater than 10 ppm) causes irritation in eyes, nose and throat, while higher exposure (greater than 25 ppm) can cause severe reactions for people with underlying pulmonary diseases like Chronic Obstructive Pulmonary Disease (COPD) or asthma. $NO_2$ reacts with water droplets in the trachea and lungs and forms droplets of nitric acid. These tiny droplets of nitric acid penetrate deeply into the lungs and causes various respiratory diseases. $NO_2$ exposure has also being associated with Sudden Infant Death Syndrome (SIDS). A detailed report of the actual accidental release of $NO_2$ and its subsequent health effect on the population has been provided. The United States Occupational Safety and Health Administration (OSHA) has set a 5 ppm workplace permissible exposure limit for $NO_2$, time averaged over an 8 h work shift. $NO_2$ also leads to the formation of ozone which is hazardous to both aquatic and terrestrial ecosystems. Current methods of quantification of $NO_2$ in the air includes gas chromatography equipped with mass spectroscopy (GC-MS), chemiluminescence, differential optical absorption spectroscopy (DOAS), laser induced fluorescence (LIF), cavity ring down spectroscopy (CRDS) and resonance enhanced multi photon ionization (REMPI).

However, these analyses can be very expensive, requiring trained experts, and having complex, bulky and non-portable instrumentation. Metal-oxide semiconductor based gas sensors can be an effective solution to the underlying limitations faced by currently used methods for measuring $NO_2$. Metal oxide materials, such as, for example, yttria stabilized zirconia (YSZ), natrium superionic conductor (NASICON), $In_2O_3$, and $WO_3$, have been used for $NO_2$ gas sensing. Among metal oxides, $WO_3$ is considered to be a good candidate for low concentration $NO_2$ sensing.

$WO_3$ is an n-type semiconductor with a band gap of 2.75 eV which is known to exist in multiple polymorphs such as tetragonal ($\alpha$), orthorhombic ($\beta$), monoclinic ($\varepsilon$ and $\gamma$), and triclinic ($\delta$). Each of these forms exhibits different electrical, optical and magnetic behaviors which are favorable for particular applications. Gas sensing property of $WO_3$ was discovered for the first time by Shaver, in 1967 when he observed a change in conductivity of $WO_3$ thin film in presence of low concentration of $H_2$. Since then n-type $WO_3$ has been used for sensing $H_2$, $H_2S$, $NO_x$, $NH_3$, $O_3$, CO, and acetone.

Some essential components of a gas sensing device are: a metal-oxide sensing layer deposited on gold or platinum interdigitated electrodes which are attached to an alumina or silicon substrate with a heater and a temperature probe to increase and control the temperature of the sensing layer. $WO_3$ film deposited on interdigitated electrodes possesses both receptor and transducer functions, where the reaction of the $NO_2$ species takes place on the $WO_3$ film (receptor function) and the adsorbed $NO_2$ changes the resistance (transducer function) of the sensing film. This change in resistance can be correlated with the concentration of $NO_2$. The response (S) for $NO_2$ is calculated as the ratio of the resistance of the $WO_3$ film on gold interdigitated electrodes at different gas concentration and is given by the following equation:

$$S = \frac{R_g}{R_a}$$

where, $R_g$ is the resistance of the film in presence of $NO_2$ and $R_a$ is the resistance of the film in air. Metal-oxide gas sensors based on this principle are one of the most studied gas sensor types because of its low cost of production, miniature size, low power consumption, and large number of applications.

The detailed mechanism of a n-type semiconductor thin film sensor is explained by Franke et. al. (Metal and metal oxide nanoparticles in chemiresistors: does the nanoscale matter?, Small 2 (2006) 36-50) which can be used as a model to define the interaction between n-type $WO_3$ and $NO_2$ FIG. 12A depicts the mechanism. At elevated temperature, oxygen from the air is adsorbed on the $WO_3$ surface. Since a constant voltage is applied externally on the $WO_3$ film, the electrons are exchanged from the conduction band of $WO_3$ to the adsorbed oxygen causing them to convert to ionosorbed species. $NO_2$ is a strong oxidizer, because of the presence of an unpaired electron in its outermost shell, which supports the formation of ionosorbed oxygen according to the following equations:

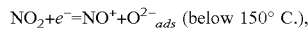

$NO_2 + e^- = NO^+ + O^{2-}_{ads}$ (below 150° C.),

$NO_2 + e^- = NO^+ + O^-_{ads}$ (150-500° C.)

This causes the formation of an electron depletion region around the individual $WO_3$ particle, also known as space-charge layer, $\Lambda_{gas}$. At the junction of two particles a larger electron depletion layer ($2*\Lambda_{gas}$) is formed causing conduction band bending of $WO_3$ and the generation of a surface potential barrier (height of band bending $qV_s$). Since the electronic conduction occurs along a percolation path via particle to particle contact, presence of the large electron depletion region hampers the electron path causing an increase in overall $WO_3$ film resistance.

The gas sensing property of $WO_3$ films strongly depends on the preparation method and the growing conditions of the film itself. Some synthesis procedures have been proposed for producing the $WO_3$ films for NO and $NO_2$ sensors. These can include spray pyrolysis, drop coating, co-precipitation, sol-gel synthesis, plasma-enhance chemical vapor deposition (PECVD), thermal evaporation, and glancing angle DC magnetron sputtering. In order to have a high productivity, low resistance, and a low power consumption sensor, the current trend is to construct the sensing elements on a chip.

The present disclosure proposes an open atmosphere flame based process also known as Reactive Spray Deposition Technology (RSDT) for the synthesis of $\gamma$-$WO_3$ films directly on gold interdigitated electrodes. The RSDT process allows the flexibility to create $\gamma$-$WO_3$ with control of the particle size, porosity and thickness of the film. The sensitivity of porous $WO_3$ increases when the particle size is below its Debye length ($L_D$) which is 25 nm. RSDT is a subset of flame spray pyrolysis which was developed for the synthesis of nanoparticles. This process can employ a broad selection of precursors compared to conventional vapor-fed flame reactors. In RSDT, nanoparticles are generated in the flame, and then are either directly deposited on the substrate as a film or collected as a nanopowder. This eliminates the intermediate steps of filtration, drying, and calcination. By incorporating a secondary spray system, nanoparticles can also be deposited on various supports such as carbon, magneli phase titania and ceria. RSDT provides complete control of the nanoparticle size, crystallinity, porosity, film thickness, and support concentration. The ability to control the substrate temperature from 20 to 1000° C. enables the use of a wide array of substrates. It is noted that the present disclosure has used RSDT for the synthesis of various nanomaterials. In studies, it has been shown that RSDT can be employed for the synthesis of $WO_3$ films with precise control of particle size, film morphology, and crystal structure. In this disclosure, RSDT has been used for the deposition of nano crystalline $WO_3$ thin films directly on a gold interdigitated electrode which is to be assembled into an $NO_2$ sensing device.

A description is hereby provided of the synthesis, fabrication and testing procedure of the $NO_2$ sensor. The microstructure of the tungsten oxide films, and the effect of the film structure, grain size, and the sensor response to the ppm level concentration of $NO_2$ is described. $NO_2$ response behavior on the tungsten oxide surface at various operating temperatures is also presented.

The properties of the $WO_3$ film was investigated by X-ray diffraction (XRD), Raman spectroscopy, the Brunauer-Emmett-Teller (BET) method, high resolution transmission electron microscopy (HRTEM), and scanning electron microscopy (SEM). The sensor response was tested from 0.17 to 5 ppm at different operating temperatures (250 to 350° C.) to determine an optimum working temperature. The sensor film was ultimately performance tested for $NO_2$ sensitivity in the 0.17 to 5 ppm range at 300° C. The sensor was further tested for stability for 300 hours in 0.5 ppm $NO_2$ in the air which is 10 times lower than the workplace permissible exposure limit (PEL) as per the Occupational Safety and Health Administration (OSHA) specification. The sensor was tested below the PEL because it is desirable for the workplace atmosphere to remain below the PEL of $NO_2$. In order to check the selectivity, the sensor was also tested for 10 ppm acetone, 100 ppm ethanol, 10 to 100 ppm $H_2$, and 10 ppm isoprene. The test data of $WO_3$ based $NO_2$ sensors prepared by RSDT has been compared with the results reported in literature.

Experimental

Synthesis of $WO_3$:

An explanation of the RSDT equipment and process is described in detail by Jain and Roller et. al. (Synthesis of nano-Pt onto ceria support as catalyst for water-gas shift reaction by Reactive Spray Deposition Technology, Appl. Catal. A: Gen. 475 (2014) 461-468; see also Processing, Activity and Microstructure of Oxygen Evolution Anodes Prepared by a Dry and Direct Deposition Technique, ECS Trans. 45 (2013) 97-106).

Figure 13:
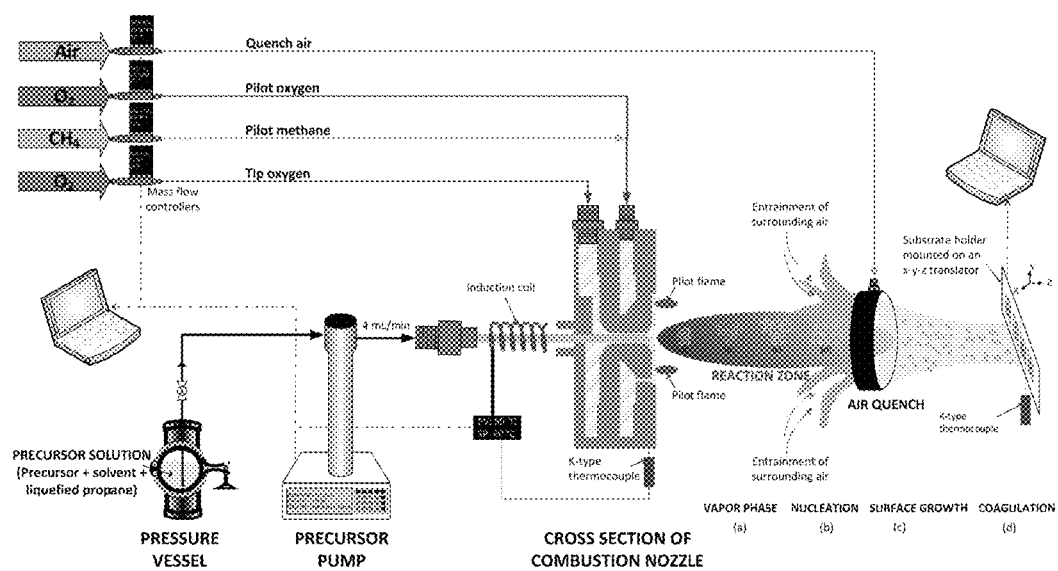
FIG. 13 shows the arrangement of the Reactive Spray Deposition Technology for direct deposition of $WO_3$ on gold interdigitated electrodes.

FIG. 13 shows the schematic of RSDT along with the cross sectional view of the combustion nozzle. Tungsten hexacarbonyl [$W(CO)_6$] was obtained from Sigma Aldrich (Catalogue #AC221040100) and was dissolved in a tetrahydrofuran (THF) (enthalpy of combustion: 2501 kJ/mol) (Fisher Scientific # SHBD3901V). The precursor was chosen based on its low decomposition temperature of 170° C.

20 wt % sulfur free liquefied propane (Airgas catalogue # PRCP350S) was added to the above to form a precursor solution resulting in a final concentration of 5 mM/L $W(CO)_6$, and 18 wt % propane. THF has a dual role of an inexpensive solvent and fuel for the combustion of the [$W(CO)_6$].

The precursor solution was filled in a syringe pump (Teledyne Isco 500D) and after heating to 50 to 60° C., it was directed through a 4 mL/min stainless steel capillary tube of 100 μm inner diameter to the combustion nozzle. Six methane-oxygen flamelets (methane and oxygen at 0.5 L/min each) surround the capillary end, which ignites the combustible precursor mist. The precursor solution was atomized by oxygen (5 L/min) and a pressure drop of 125 psi was maintained at the exit point of the nozzle. At 10 cm from the combustion nozzle, an circular air quench ring (Exair, Super Air Wipe) with a compressed air flow rate of 70 L/min was positioned.

The distance between the combustion nozzle and the air quench is considered the reaction zone and the length of the reaction zone is proportional to the residence time of the nano-particles in that zone. Adjusting the length of the reaction zone and the flow rate of compressed air gives unique conditions to obtain an assortment of crystalline structures and phases of the material. This also enables "nano quenching" thereby limiting the particle size growth in the flame. Two silicon plates (Nova electronic materials item #8289) and two gold interdigitated electrodes on alumina base (Electronic design center-Case Western Reserve University item #102) were used as substrates.

Silicon plates were used to evaluate the film thickness since they can be easily fractured and can be mounted at 90° on a SEM stub. Gold interdigitated electrodes on alumina base (Electronic design center-Case Western Reserve University item #102) were used as substrates for the gas sensing. This thick film printed electrode consists of interdigitated gold deposits on a 0.6 mm thick alumina substrate. The dimensions of the alumina base is 15 mm by 15 mm. The gold thick film screen printed electrode digits are 250 μm wide with 250 μm spacing between them. The gold digits are connected with a pair of gold bonding pads which allow wires to be threaded through them as an aid for electrical connection.

Prior to $WO_3$ deposition, the electrode was cleaned with acetone, methanol and deionized water, in order and dried in an air oven operating at 80° C. for 1 hour. The four substrates were mounted on a stainless steel substrate holder, which was placed on an x-y-z platform. This enabled the substrates to move along a serpentine path in front of the flame to ensure even coating of $WO_3$ on the substrates. The total deposition area was 25 $cm^2$. The samples were annealed in the air at 500° C. for 5 h in an oven to stabilize the $WO_3$ film. The characterization and gas sensing measurements were performed on the post annealed samples.

Characterization:

XRD patterns of $WO_3$ films directly deposited on gold interdigitated electrodes were recorded in the air at 25° C. on a Bruker D8 advanced powder diffractometer using CuKα radiation. The scans were taken in the 2θ range of 20-55° with a step size of 0.02° and time per step of 5 seconds.

Raman spectra were obtained in air at 25° C. in the spectral range between 100 and 1200 $cm^{-1}$ with a Renishaw Ramascope micro-Raman spectrometer fitted with a reflected light microscope using a 50 mW laser (514.5 nm) and exposure time of 10 s. Laser power delivered to the sample was set at 20% (10 mW) to avoid sample damage. Instrument alignment was optimized using a 521 $cm^{-1}$ signal of a silicon wafer.

Raman measurements for $WO_3$ is well known to provide structural and phase information of $WO_3$ material. The surface area of $WO_3$ particles was calculated by the Brunauer-Emmett-Teller (BET) method using $N_2$ sorption experiments on a Micromeritics ASAP 2020 BET system. Samples were degassed for 12 h prior to $N_2$ sorption measurements. For obtaining the samples for BET, a separate experiment was performed in which, $WO_3$ nanoparticles powder was directly collected on a stainless steel substrate holder. The deposit was scrapped off using a plastic spatula and analyzed for $N_2$ sorption experiments. SEM micrographs were collected on an FEI ESEM Quanta 250 with a field emission gun at 5 kV accelerating voltage and 8 mm working distance. For determining the cross sectional thickness of the film, the silicon substrate with $WO_3$ film was fractured, and mounted on a 90° aluminum stub. The sample was gold sputter coated prior to imaging under SEM. TEM micrographs and selected area diffraction pattern (SADP) of $WO_3$ particles were obtained on a 120 kV FEI Tecnai T12 S/TEM with a $LaB_6$ source.

HRTEM micrographs were obtained on a 200 kV FEI Metrios TEM with an X-FEG source. 300 mesh Cu grids coated with holey/thin carbon films (Pacific Grid Tech Cu-300HD) were used. A small portion of the film was scraped off from the gold interdigitated electrodes and was sonicated with ethanol. Few drops of the resulting solution were dropped on the grids and air dried before they were placed in the ultra-high vacuum (UHV) chamber of the TEM.

Figure 14:
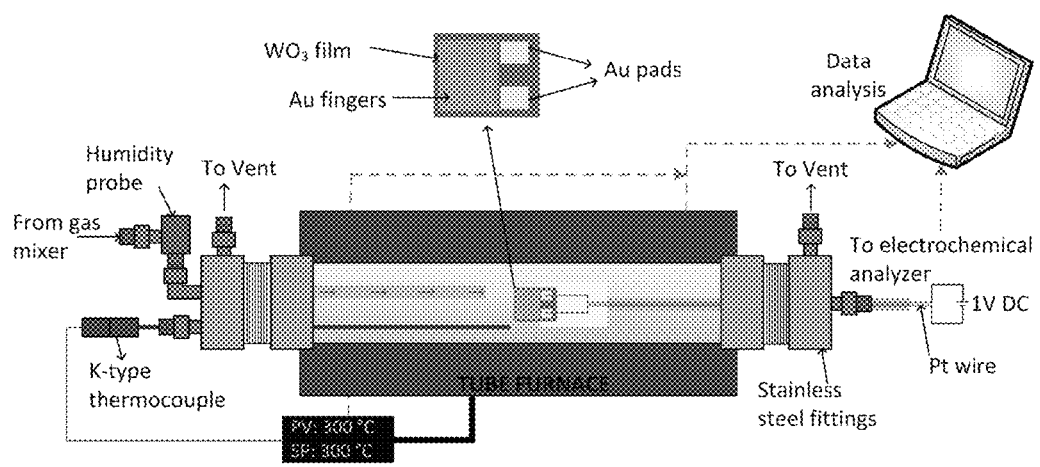
FIG. 14 shows a schematic of the gas sensing test setup.

Gas Sensing Test:

Gas sensing tests were performed in a dynamic flow system, implemented in the laboratory as shown in FIG. 14.

Prior to gas sensing, the electrode was annealed in the air at 500° C. for 5 h in an electric oven to stabilize the $WO_3$ film. A $WO_3$ coated gold interdigitated electrode was introduced in a quartz cylindrical test chamber (10 cm length and 3.2 cm inner diameter) which was wrapped by a high temperature nozzle band heater (McMaster Carr item #3594K981). The ends of the test chamber were sealed by stainless steel fittings. Several ports were introduced in the test chamber for (1) gas inlet, (2) 2 gas outlets, and (3) standard k-type thermocouple to monitor temperature.

Gas flow to the furnace was controlled by Environics Series 4040 Computerized Gas Dilution System with an option for precise humidification control (0 to 100% relative humidity). The presence of 2 gas outlets in the test chamber allowed a precisely controlled change in the atmosphere of the test chamber, as soon as the gas concentration is changed from $NO_2$ to pure air and vice versa. Dry synthetic air (Airgas #AI UZ300) was used as a diluent gas and 10 ppm $NO_2$ in the air (Airgas #X02AI99C15A2520) was used for adjusting the $NO_2$ concentration.

Humidity level of 100% r.h. was maintained throughout the tests as measured by a calibrated hygrometer (Vaisala HMT 337). Flow rate of 1.5 L/min was maintained in the test chamber. For the two probe amperiometric measurements, the $WO_3$ coated electrode was connected with two Pt wires (99.9% metals basis) (0.127 mm diameter) (Alfa Aesar#F20X038) and connected with a CHI instrument's electrochemical analyzer (CHI6116E).

Current (I) was measured as a function of time and gas flow concentration at a constant 1 V DC power supply. Resistance (R) was calculated by applying Ohm's law (R=V/I). The data was collected every 100 ms.

Figure 15A:
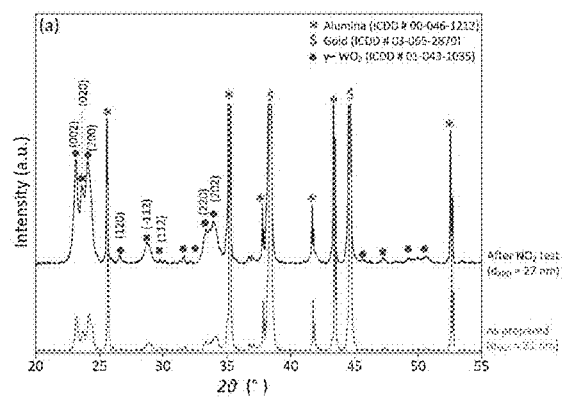
FIGS. 15A-15B: (a) X-ray diffraction, (b) Raman spectroscopy of $WO_3$ film directly deposited on gold interdigitated electrodes, both pre and post $NO_2$ test showing that there is no change in the structure of the film.

Results: Structural Properties:

X-Ray Diffraction (XRD):

FIG. 15A shows the XRD pattern of the $WO_3$ film coated on gold interdigitated electrodes pre and post $NO_2$ tests.

The $WO_3$ film showed the monoclinic structure and was indexed to ICDD#01-043-1035. The characteristic main peaks for γ-$WO_3$ were seen at the 2θ value of 23.2°, 23.6° and 24.4° and can be associated with the (002), (020) and (200) reflections, respectively.

Average crystallite size of $WO_3$ was calculated from X-ray line broadening by Debye Scherrer's method and was 21 nm on the as prepared sample, and 27 nm on the post $NO_2$ test samples. As seen from the XRD pattern, there was an increase in the intensity of the $WO_3$ film post $NO_2$ tests. This could be due to the increase in crystallinity of the $WO_3$ particles under the high temperature of testing. However no change in the overall structure of the film was observed verifying that the film was stable under the $NO_2$ test conditions.

Raman Spectroscopy:

A Raman spectroscopy technique was used for identifying the phases in the $WO_3$ film since this technique is known to give the "fingerprint" of $WO_3$ material.

Figure 15B:
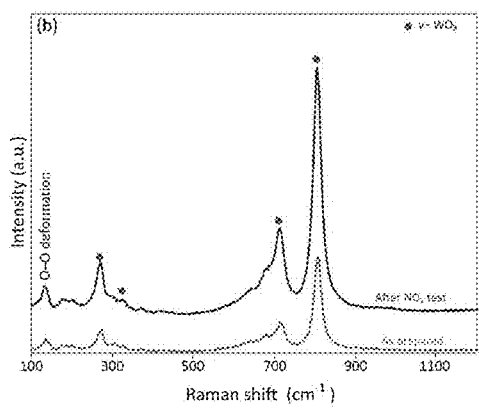

FIG. 15B shows the Raman spectroscopy results of the $WO_3$ film directly deposited on gold interdigitated electrodes, both pre and post $NO_2$ tests. The strongest peaks were seen at 808 and 715 $cm^{-1}$ which are similar to those of the monoclinic γ-$WO_3$. A relatively strong peak was observed below 150 $cm^{-1}$ for all the samples which indicates the O—O deformation mode. Intensity of the $WO_3$ film after $NO_2$ sensing has increased, consistent with the XRD results. On the basis of XRD and Raman spectroscopy results, it can be concluded that the structure of the $WO_3$ film in this study is monoclinic γ phase.

Electron Microscopy (SEM and TEM):

FIGS. 16A-16C show the SEM micrographs of the $WO_3$ film as deposited on a Si wafer and gold electrode.

The Si wafer was the chosen as a substrate because it can be easily fractured which enables the examination of the $WO_3$ film cross section. From FIG. 16A the film thickness was measured to be 2.5 μm.

FIG. 16B shows the $WO_3$ film directly deposited on the gold interdigitated electrode. Uniformly coated gold lines with $WO_3$ can be seen and it can be inferred that the film formation is conformal in nature.

From FIG. 16C it can be inferred that the $WO_3$ film surface is rough and porous with the formation of some agglomerates around 5-10 μm wide. Various open pores could be seen which is advantageous for the diffusion of gases in the bulk of the film. The total $WO_3$ deposition area on the gold electrodes was 97.5 $mm^2$. The surface to volume ratio of the $WO_3$ film was 400 $mm^{-1}$. The images indicate high quality porous $WO_3$ films deposited by RSDT without any cracks, voids, dense regions or surface abnormalities.

FIGS. 16D-16E show the bright field TEM and HRTEM micrographs of the $WO_3$ particles.

Various oval shaped particles can be seen. From a TEM point analysis, a particle size ($d_{TEM}$) distribution ranging between 20-30 nm was observed. No evidence of sintering of the nanoparticles was found which is attributed to the use of air quench in RSDT. The selected area diffraction patterns (SADP) of $WO_3$ is shown in the inset of FIG. 16D.

The brightest diffraction ring corresponds to the (002), (220) and (114) planes. FIG. 16E shows the HRTEM micrograph of one of the particle with the lattice fringes clearly visible. The lattice fringe spacing corresponds to the (002) plane of γ-$WO_3$.

BET Surface Area:

$N_2$ sorption measurements were performed for the $WO_3$ powder and the surface area was calculated by the BET method. The BET surface area was calculated as 46 $m^2/g$.

An average particle diameter was estimated using the BET surface area and the density of $WO_3$ (7.16 g/cc) by making the assumption that the particles are uniformly sized spheres. Particle diameter ($d_{BET}$) was calculated to be 18 nm.

Response Dependence on Temperature:

The $WO_3$ film was tested for $NO_2$ response in the range of 0.17 ppm to 5 ppm between 275 to 350° C. to establish the relationship between $NO_2$ concentration and temperature, and to determine the working temperature at which the best response can be obtained.

FIG. 17A shows this relationship. It can be seen that as the temperature is increased, the response increases till it reaches the maximum value at 300° C. If the temperature is further increased, the response is reduced. This could be due to increased desorption of $NO_2$ at high temperature which reduces the concentration of ionosorbed oxygen at the $WO_3$ surface.

Gas Sensing Results:

FIG. 17B shows the normalized response-recovery curve versus time for the $NO_2$ concentration ranging from 0.17 to 5 ppm in the air at 300° C. and 100% relative humidity. The measurable limit for the tests was 0.17 ppm. The response increases as the concentration of $NO_2$ is increased. This is because of the increased adsorption of $NO_2$ molecules at higher $NO_2$ concentration. The adsorption and desorption of the $NO_2$ molecules on the $WO_3$ film takes place simultaneously and is a reversible process.

During the response stage, adsorption is higher than desorption and the resistance of the film increases. This is because $NO_2$ diffuses through the porous $WO_3$ film and oxidizes the $WO_3$ surface thereby increasing the ionosorbed oxygen concentration of the film. This causes an increase in electron scattering sites. $NO_2$ also captures electrons from the conduction band of $WO_3$ causing the formation of an electron depletion region, triggering an increase in its resistance.

It was seen that the sensor response was spontaneous as the gas concentration in the test chamber was changed from pure air to $NO_2$ in the air. The response time was calculated to be 7.2 s. The sensor stabilized at the maximum value of resistance, very quickly. At this point, the adsorption rate is equal to the desorption rate. Maximum adsorption had taken place at that particular analyte concentration and the $WO_3$ film was in equilibrium with the $NO_2$ molecules. Recovery of the sensor started when pure air was switched back to the test chamber.

At this point, adsorption was nil and desorption was the only process which was taking place. Presence of two vents in the test chamber expedited the exchange of the gas atmosphere. However it was seen that desorption was still slower than adsorption. A drift can be seen when the resistance of the film is measured in air after exposure to $NO_2$ at different concentrations. This is caused because of incomplete recovery during the 5 minute of recovery phase.

Stability Tests:

Stability tests of the $WO_3$ films were conducted for 300 h at 0.5 ppm $NO_2$ in the air at 300° C. and 100% relative humidity which is 10 times lower than the workplace permissible exposure limit (PEL) as per the Occupational Safety and Health Administration (OSHA) specification. The sensor was tested below the PEL because it is desirable for the workplace atmosphere to remain below the PEL of $NO_2$. 0.5 ppm $NO_2$ was switched on every 5 minutes (response) followed by 5 minutes of pure air (recovery). Resistance of the film was measured every 100 ms to record the response and recovery cycle (response+recovery time=10 min).

A total of 2000 response-recovery cycles were recorded.

Figure 18:
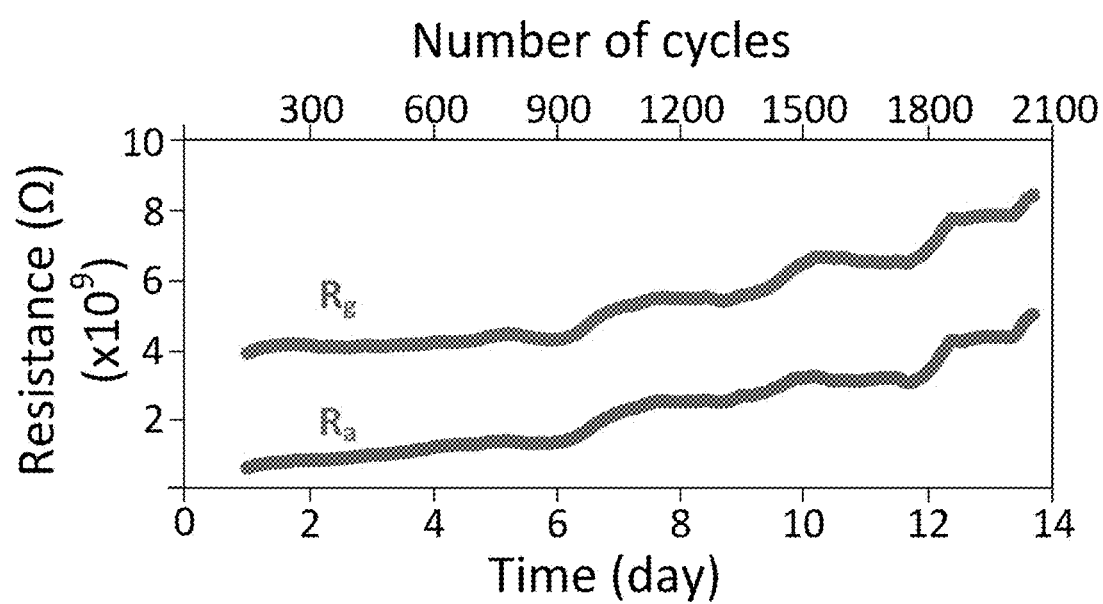
FIG. 18 shows stability tests for a $WO_3$ sensor conducted for 300 h at 0.5 ppm $NO_2$ in the air at 300° C. and 100% relative humidity.

FIG. 18 shows the resistance over time for $WO_3$ film in pure air ($R_a$) and 0.5 ppm $NO_2$ in air ($R_g$) respectively.

The resistance is calculated as the moving average for the data collected every 24 h. It can be seen that the sensor is stable till day 6 (around 150 h). From day 6 to 14 (150-300 h) the sensor began to degrade possibly due to the growth of the $WO_3$ nanoparticles. This shows that maximum degradation of the sensor occurred after day 8 (around 200 h) as evident from the fluctuation of resistance.

Figure 19:
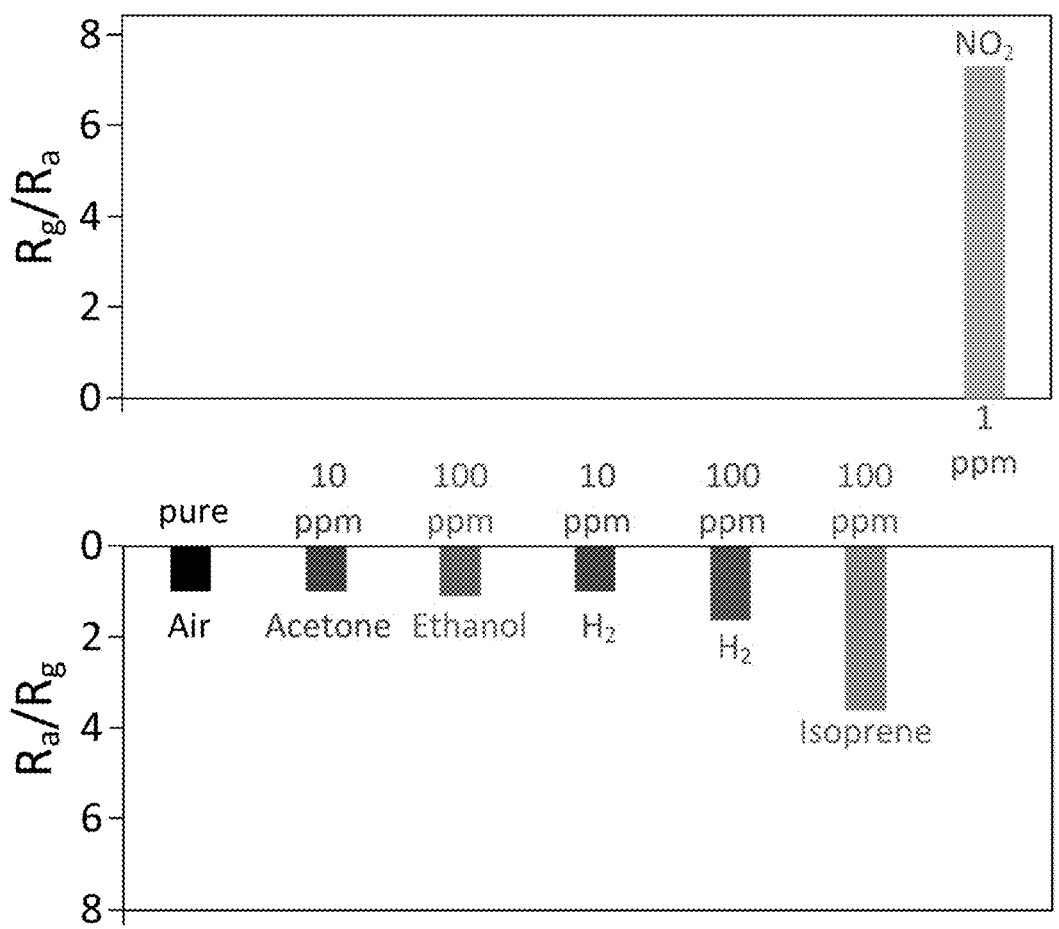
FIG. 19 shows $NO_2$ response as compared to other reducing analytes.

Selectivity:

The response of 1 ppm $NO_2$ was compared with 10 ppm acetone, 100 ppm ethanol, 10-100 ppm $H_2$ and 10 ppm isoprene at 0.5 ppm $NO_2$ in air at 300° C. and 100% relative humidity. This is shown in FIG. 19.

It can be seen that the sensor had negligible response for acetone, ethanol and 10 ppm $H_2$. However the response is significant for 100 ppm $H_2$ and 10 ppm isoprene. Isoprene and $H_2$ are some of the major component exhaled from the human breath. Typical values of isoprene in the breath of a healthy human range from 0.012 to 0.58 ppm, while $H_2$ ranges from 10-20 ppm.

Discussion:

On the basis of the characterization and gas sensing results, one can conclude that RSDT can be used for the synthesis of $NO_2$ sensing films directly on gold interdigitated electrodes. Based on previous work on $WO_3$, and a review of the literature, it can be shown that the characteristics of the sensing device that are important for good performance are: (1) high porosity of the sensing film, (2) particle size of the sensing film smaller than the Debye length ($L_D$), a characteristic of the semiconductor material, which is 25 nm for $WO_3$, (3) film thickness, (4) absence of impurities in the test atmosphere, (5) test chamber volume, and (6) time required for the exchange of gases in the test chamber.

In this discussion, the importance of these factors is identified and shows that the gas sensing test data presented in this Example adheres to these requirements. The comparison is shown between the RSDT synthesized sensors and the sensors synthesized by other techniques as shown in Table 2 above.

Since the sensing is an adsorption-desorption process, gas diffusion through the film plays a major role in the sensor performance. The sensing film must be porous to effectively allow the diffusion process and extend the reaction between $NO_2$ and oxygen from the surface to the bulk. By assuming steady state conditions, it can be interpreted that the $NO_2$ concentration decreases with the film depth which causes the formation of various degree of reactions at different depths of the film. The resistance change data recorded by the electrochemical analyzer averages the resistances by providing the overall resistance change of the film. It would be beneficial to eliminate this variation. Film porosity, thickness, microstructure, and the electrode pattern are some factors which govern this variation. From the SEM micrographs in FIG. 16C it can be seen that the $WO_3$ film synthesized by RSDT is highly porous and uniform.

Gas sensing response is dependent on the particle size of the sensing film. Smaller particles and increased surface area (higher surface to volume ratio) provides larger number of sites for the surface reaction to occur. At the same time, reducing the particle radius below $\Lambda_{gas}$, will converge the electron depletion layer ($2\Lambda_{gas}$) and the electrical conduction will be dominated by the presence of adsorbed $NO_2^-$. $\Lambda_{gas}$ depends on the Debye length ($L_D$) of the material which is 25 nm for $WO_3$. Researchers have described the relationship between gas sensitivity and particle size with respect to the Debye length ($L_D$). When the particle size is smaller than $L_D$, the ionosorbed oxygen will extract the electrons from the $WO_3$ particle causing an increase in film resistance. It was also shown by researchers that the sensitivity of 10 ppm $NO_2$ towards $WO_3$ particles were three fold higher when the particle size was smaller than 25 nm as compared to particles larger than 33 nm. In this Example, the $WO_3$ particle size were in the range 20-30 nm as determined by the TEM point analysis in FIG. 16D. BET surface area measurements revealed the average particle diameter ($d_{BET}$) to be 18 nm.

Working temperature is an important factor responsible for the performance of the sensor since sensing is an adsorption desorption process which is also influenced by kinetics. At low working temperature, the activation barrier for the generation of ionosorbed oxygen is higher, while at high temperature, the desorption of $NO_2$ exceeds adsorption resulting in lower response. Hence the optimum temperature at with balance kinetics and desorption is essential. In this Example, the highest response was obtained at 300° C.

Selectivity with other gases is a concern for a sensor to be commercially viable, which can lead to false alarm or incorrect gas concentration determination. In this study, it was found that the $WO_3$ film was responsive towards 10 ppm isoprene and 100 ppm $H_2$, while the response towards 10 ppm acetone, 100 ppm ethanol and 10 ppm $H_2$ was negligible.

The tests were performed in 100% relative humidity and sensitivity towards $H_2O$ was not observed. There are various methods suggested in the literature to discriminate the interference towards these gases. A common approach is to utilize a sensor array with various sensor electrodes to filter out the response from the interfering analytes. Another method is to use filters upstream of the electrode to filter out the gases. One such activated charcoal filter is used by Figaro Inc. in their commercial CO sensor—TGS5042.

Since the sensor response is a diffusion driven process, it can be applied to improve the selectivity. Porous layers in which gases may have different diffusion coefficient can be directly deposited on the sensing layer. These layers acts as molecular sieves to reject the interfering gases. Description of these porous layer filters have been provided in details in the literature.

The long recovery time and the drift of the metal oxides based sensors have been long recognized and various suggestions to counter this limitation have been proposed. From the gas sensing tests in FIG. 17B, a drift can be seen when the resistance of the film is measured in the air after exposure to $NO_2$ at different concentrations. This is caused because of incomplete recovery during the 5 minute of recovery phase. As a gas molecule is chemically adsorbed on the surface of $WO_3$, it is in thermal equilibrium and resides at the bottom of the potential well (minimum potential energy).

In order to desorb from the surface, the only driving force it experiences is the diffusion caused by the change in the concentration of gases in the test chamber on switching to pure air. However, this energy is not sufficient and causes a long delay to achieve complete desorption. Further thermal or electrical energy is required to expedite this adsorption process. Different ways are suggested in literature to eliminate sensor drift.

These include, for example, using high-speed gas-switching system and smaller volume test chamber for enabling quicker gas exchange, pre exposing the sensing film to the analyte for a set period of time, use of mathematical function and modeling to pre-estimate the steady state conditions and remove the time lag, use of multiple sensing electrodes in different test chamber to alter between response and recovery, use of neural network algorithm for the sensor to "self-learn," use of strong negative field to electro-desorb the residual analyte molecules to "refresh" the sensor, and by illuminating the sensor with ultra-violet (UV) light.

This Example used a two vent test chamber to expedite the atmosphere change. The test chamber volume was 85 cc. It is noted that one can develop a prototype sensing device with a volume of 0.5 cc which will further eliminate this issue.

Conclusions:

In this study RSDT has been evaluated as a direct deposition technique for the synthesis of γ-$WO_3$ film for ultra-low $NO_2$ sensing.

Nano-quenching was used to optimize the particle size and film morphology to tailor the film towards superior $NO_2$ sensing performance. A main objective was to correlate the influence of the synthesis process, and the resultant structural properties of the γ-$WO_3$ film with the $NO_2$ gas sensing performance.

These properties have been highlighted, and their influence on the $NO_2$ sensing which will provide a platform for developing better sensors with improved performance compared to the currently used sensors. The reasons for the high response can be attributed to a number of factors, such particle size, porosity and pore size, and film thickness, all precisely controlled by the RSDT.

Some conclusions can be made from this Example:

1) A RSDT synthesized $WO_3$ film based $NO_2$ sensor was responsive in the 0.17 to 5 ppm range, when tested at 300° C.

2) Response time was 7.2 s and recovery time was greater than 5 minutes. The response time was better than the $WO_3$ sensors synthesized by the traditional wet chemistry processes from literature.

3) The response was highest at the working temperature of 300° C.

4) The $NO_2$ sensors gave a steady response till 150 hours of continuous performance and started to degrade after 200 hours possibly due to increase in particle size.

5) Interference was negligible with 10 ppm acetone, 100 ppm ethanol, 10 ppm $H_2$ and humidity; however, it was significant with 10 ppm isoprene and 100 ppm $H_2$.

6) Response and recovery of the sensor is caused by adsorption and desorption respectively. Hence, recovery time can be improved by expediting the desorption step.

7) $WO_3$ particle size of less than 25 nm attributes to better charge transfer which translates to superior $NO_2$ sensitivity.

Example 2:—Ultra-Low Acetone Detection by Epsilon $WO_3$ Synthesized by Reactive Spray Deposition Technology Highlights:

1. Monoclinic epsilon $WO_3$ thin film was synthesized by a single step flame based process.

2. The $WO_3$ film was tested with 0.2 to 5 ppm acetone in air at 400° C.

3. The structural properties of the $WO_3$ was correlated with the gas sensing data.

4. The $WO_3$ film showed quicker response time than similar films synthesized by traditional processes.

5. Test and stability data shows that performance improvements that approach 100% efficiency can be made.

A metastable monoclinic epsilon tungsten oxide ($WO_3$) film based acetone sensor was developed by the flame based process called Reactive Spray Deposition Technology (RSDT) depositing directly on gold interdigitated electrodes. The sensitivity of this acetone sensor was measured at the parts per million (ppm) level, (0.2 to 5 ppm in air) at 400° C. The sensors showed a relatively fast response time (around 7 seconds) to acetone vapor. The stability of the sensor was evaluated for 450 hours in 0.5 ppm $NO_2$ in air (2700 response-recovery cycles). The sensor was stable up to 10 days (around 250 hours) of continuous operation and degraded between 250 to 450 hours. The selectivity of the sensor was tested in 90% relative humidity, 10 ppm $H_2$, 8 ppm CO, and 0.2 ppm ethanol. The morphology and surface properties of the $WO_3$ film were investigated with XRD, Raman spectroscopy, SEM, and TEM. In addition, operando XRD experiments were performed at the condition of the acetone tests to confirm the stability of the structure. The test data of the $WO_3$ based acetone sensors prepared by RSDT was compared with the results reported in literature.

Introduction:

In this Example, an open atmosphere flame based process also known as Reactive Spray Deposition Technology (RSDT) for the synthesis of ε-$WO_3$ films directly on gold interdigitated electrodes is provided.

The RSDT process allows the flexibility to create ε-$WO_3$ with control of the particle size, porosity and thickness of the film. The sensitivity of porous $WO_3$ increases when the particle size is below its Debye length ($\lambda_0$) which is 25 nm. It has been shown that RSDT can be employed for the synthesis of γ-$WO_3$ films with precise control of particle size, film morphology, and crystal structure. In this Example, RSDT has been utilized for the deposition of nano-crystalline $WO_3$ thin films directly on a gold interdigitated electrode which is to be assembled into an acetone sensing assembly/device.

This Example provides a description of the synthesis, fabrication and testing procedure of the acetone sensor. The microstructure of the tungsten oxide films, and the effect of the film structure, grain size, and the sensor response to the ppm level concentration of acetone is also described. Acetone response behavior on the tungsten oxide surface at various operating temperatures will also be presented.

The properties of the $WO_3$ film was investigated by X-ray diffraction (XRD), Raman spectroscopy, transmission electron microscopy (HRTEM), and scanning electron microscopy (SEM). The structure of the $WO_3$ film was also probed by operando XRD studies at the condition of testing. The sensor film was ultimately performance tested for acetone sensitivity in the 0.17 to 5 ppm range at 400° C. The sensor was further tested for stability for 500 hours in 0.5 ppm acetone in air which is substantially the same as the breath acetone concentration of a healthy individual. The sensor was tested at this concentration because it is desirable that the breath acetone concentration remain below 0.5 ppm which is the diabetes threshold limit.

In order to check the selectivity, the sensor was also tested for humidity, 10 ppm $H_2$, 0.2 ppm ethanol, and 8 ppm CO. The test data of $WO_3$ based acetone sensors prepared by RSDT was compared with the results reported in literature.

Experimental

Synthesis of $WO_3$:

An explanation of the RSDT equipment and process has been described in detail by Jain and Roller (Referenced in Example 1). Tungsten hexacarbonyl [$W(CO)_6$] was obtained from Sigma Aldrich (Catalogue #AC221040100) and was dissolved in a tetrahydrofuran (THF) (enthalpy of combustion: 2501 kJ/mol) (Fisher Scientific # SHBD3901V).

The precursor was chosen based on its low decomposition temperature of 170° C. Sulfur free liquefied propane (enthalpy of combustion: 2202 kJ/mol) (Airgas catalogue # PRCP350S) was added to the above to form a precursor solution resulting in a final concentration of 4.9 mmol/L $W(CO)_6$, and 18 wt % propane. THF has a dual role of an inexpensive solvent and fuel for the combustion of the [$W(CO)_6$]. Propane helps in atomization by increasing the pressure drop between the needle and the point of exit of the solution, thereby splitting the solution in tiny droplets approximately 15 μm in diameter as measured by Malvern Instrument's Spraytec laser diffraction system. The increase in surface area of the overall droplets helps in efficient combustion of the precursor.

The precursor solution was filled in a syringe pump (Teledyne Isco 500D, Lincoln Nebr.) and directed at 4 mL/min to a series of stainless steel tubes of varying diameters: 0.025 cm inner diameter 316 stainless steel tube which is brazed to a capillary of 100 μm inner diameter (Vita Needle company). An Omega k-type thermocouple was placed at the junction of the tube and capillary, the temperature of which is maintained at 170° C. by means of an induction coil wrapped upstream of the flow of precursor solution based on designs of experiments to create nanometer sized Pt particles of 1 to 3 nm. This caused the temperature of the precursor solution at the exit point to be 50 to 60° C. and a pressure drop of 90-110 psi.

The combined effect of liquefied propane, temperature, and reduction of diameter of the tube, causes the solution to shift into the supercritical regime and formation of submicron size droplets. Six methane-oxygen flamelets (methane at 0.42 L/min and oxygen at 0.55 L/min) surround the capillary end, and ignites the combustible precursor mist. The precursor solution was atomized by oxygen (5 L/min). A circular air quench ring (Exair, Super Air Wipe®) with a compressed air flow rate of 76.8 L/min was positioned at 10 cm from the combustion nozzle. The distance between the combustion nozzle and the air quench is considered the reaction zone and the length of the reaction zone is proportional to the residence time of the nano-particles in that zone. Adjusting the length of the reaction zone and the flow rate of compressed air gives unique conditions to obtain different phases and crystalline structures of the material. This also enables "nano-quenching" thereby limiting the particle size growth in the flame.

A gold interdigitated electrode on alumina base (Electronic design center-Case Western Reserve University item #102) was used as a substrate. This thick film printed electrode consists of interdigitated gold deposits on a 0.6 mm thick alumina substrate. The dimensions of the alumina base is 15 mm by 15 mm. The gold thick film screen printed electrode digits are 250 μm wide with 250 μm spacing between them. The gold digits are connected with a pair of gold bonding pads which allow wires to be threaded through them as an aid for electrical connection. Prior to $WO_3$ deposition, the electrode was cleaned with acetone, methanol and deionized water, in order and dried in an air oven operating at 80° C. for 1 h. The substrate was mounted on a stainless steel block and, placed on a x-y-z platform.

This substrate platform can be moved along a serpentine path in front of the flame to deposit on a larger area if required, however because of the small area of deposition, this motion was not required. The total deposition area was only 2.25 $cm^2$. Post deposition, the sample was annealed in the air at 500° C. for 5 hours in an oven to stabilize the $WO_3$ film. In a separate experiment, blank silicon plates (Nova Wafers, catalogue #8289) were used as substrates, for the evaluation of the film thickness since they can be easily fractured and can be mounted at 90° on an aluminum SEM stub. The characterization and gas sensing measurements were performed on the post annealed samples.

Role of Air Quench:

As discussed previously, quenching plays a very important role in obtaining the metastable monoclinic ε phase of $WO_3$. This was achieved by using the air quench in RSDT. By using air quench, the $WO_3$ particles were cooled from 500° C. to 30° C. in 7 ms.

With this rapid cooling, the $WO_3$ particles did not get enough time to freeze in their stable state, and it also caused the formation of stresses in the $WO_3$ structure. Detailed description of the air quench has been provided which will be briefly revisited here. The air quench is a circular ring with an internal annular chamber. Compressed air at room temperature enters two diametrically opposite nozzles and is directed into that chamber. The chamber has a narrow opening through which the air adopts the coanda profile and flows along the angled surface of the air quench. This also creates a low pressure region behind the air quench causing the entrainment of the surrounding air into the primary air stream.

Figure 20:
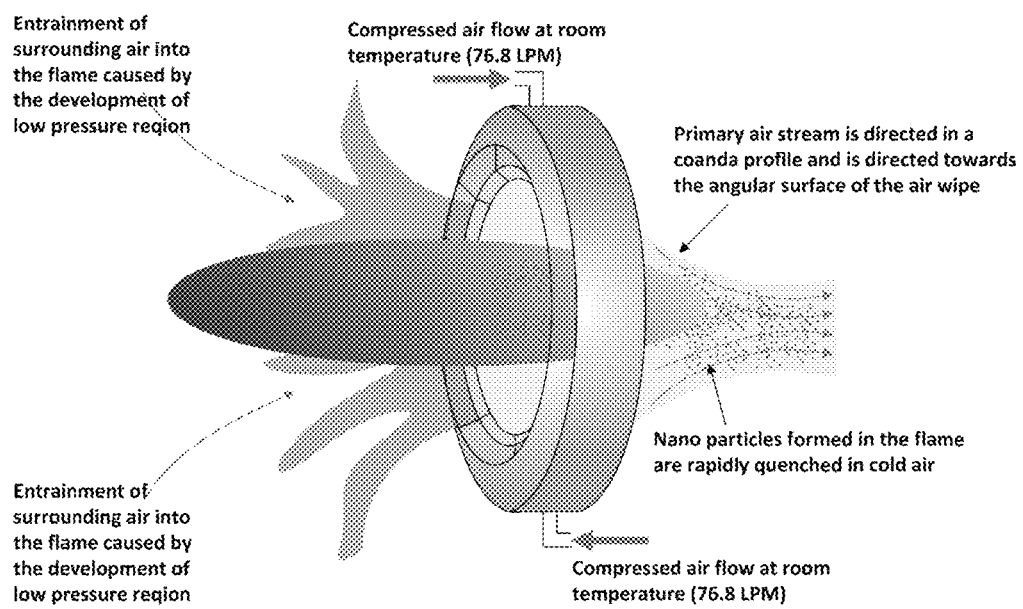
FIG. 20 shows a schematic of the air quench in RSDT.

A 360° cone of cold air is formed which cools the nanoparticles instantly and prevents growth, agglomeration, and sintering, thereby keeping the particle size small and increasing the active surface area. The distance between the combustion nozzle and the air quench is considered the reaction zone and the length of the reaction zone is proportional to the residence time of the nanoparticles in that zone. Adjusting the length of the reaction zone and the flow rate of compressed air gives unique conditions to obtain an assortment of phases and structures of $WO_3$. In this Example the reaction zone was set at 10 cm. A schematic of the air quench is shown in FIG. 20.

Characterization:

XRD patterns of $WO_3$ films directly deposited on gold interdigitated electrodes were recorded in the air at 25° C. on a Bruker D8 advanced powder diffractometer using CuKα radiation. The scans were taken in the 2θ range of 20 to 55° with a step size of 0.02° and time per step of 5 s. Operando XRD was also performed at the conditions of the acetone tests, from room temperature till 500° C. both in air and air/acetone mixture to evaluate the phase transformation during the sensing process. For this purpose, a fresh sample was prepared with the identical experimental conditions of the test sample.

The sample was placed in a high temperature Anton Paar HTK1200 heating stage in the XRD. Heating rate of 5°

C./min was used Raman spectra were obtained in air at 25° C. in the spectral range between 100 and 1200 cm$^{-1}$ with a Renishaw Ramascope micro-Raman spectrometer fitted with a reflected light microscope using a 50 mW laser (514.5 nm) and exposure time of 10 s. Laser power delivered to the sample was set at 20% (10 mW) to avoid sample damage. Instrument alignment was optimized using a 521 cm$^{-1}$ signal of a silicon wafer. Raman measurements for $WO_3$ is well known to provide structural and phase information of $WO_3$ material.

The surface area of $WO_3$ particles was calculated by the Brunauer-Emmett-Teller (BET) method using $N_2$ sorption experiments on a Micromeritics ASAP 2020 BET system. Samples were degassed for 12 h prior to $N_2$ sorption measurements. For obtaining the samples for BET, a separate experiment was performed in which, $WO_3$ nanoparticles powder was directly collected on a stainless steel substrate holder. The deposit was scrapped off using a plastic spatula and analyzed for $N_2$ sorption experiments. SEM micrographs were collected on an FEI ESEM Quanta 250 with a field emission gun at 5 kV accelerating voltage and 8 mm working distance.

For determining the cross sectional thickness of the film, the silicon substrate with $WO_3$ film was fractured, and mounted on a 90° aluminum stub. TEM micrographs and selected area diffraction pattern (SADP) of $WO_3$ particles were obtained on a 120 kV FEI Tecnai T12 S/TEM with a $LaB_6$ source. 300 mesh Cu grids coated with holey/thin carbon films (Pacific Grid Tech Cu-300HD) were used. A small portion of the film was scraped off from the gold interdigitated electrodes and was sonicated with ethanol. Few drops of the resulting solution were dropped on the grids and air dried before they were placed in the ultra-high vacuum (UHV) chamber of the TEM.

Gas Sensing Test:

Gas sensing tests were performed in a dynamic flow system, implemented in the laboratory as shown in FIG. 14. Prior to gas sensing, the electrode was annealed in the air at 500° C. for 5 h. in an electric oven to stabilize the $WO_3$ film. A $WO_3$ coated gold interdigitated electrode was introduced in a quartz cylindrical test chamber (10 cm length, 3.2 cm inner diameter, volume of 80 cc) which was wrapped by a high temperature nozzle band heater (McMaster Carr item #3594K981).

The ends of the test chamber were sealed by stainless steel fittings. Several ports were introduced in the test chamber for (1) gas inlet, (2) two gas outlets, and (3) standard k-type thermocouple to monitor temperature. Gas flow to the furnace was controlled by Environics Series 4040 Computerized Gas Dilution System. The presence of two gas outlets in the test chamber allows a precisely controlled change in the atmosphere of the test chamber, as soon as the supply gas concentration is changed from acetone to pure air and vice versa. Dry synthetic air (Airgas #AI UZ300) was used as a diluent gas and 10 ppm acetone in air (Airgas # X02AI99C15A38K3) was used for adjusting the acetone concentration.

Flow rate of 1.5 L/min was maintained in the test chamber, because it is same as the human expiratory flow rate and it is expected that the results of this study could lead one to develop a sensor for human breath analysis. For the two probe amperiometric measurements, the ε-$WO_3$ coated electrode was connected with two Pt wires (99.9% metals basis) (0.127 mm diameter) (Alfa Aesar#F20X038) and connected to a CHI instrument's electrochemical analyzer (CHI6116E). Current (I) was measured as a function of time and gas flow concentration at a constant 1 V DC power supply. Resistance (R) was calculated by applying Ohm's law (R=V/I). The data was collected every 100 ms.

Figure 21:
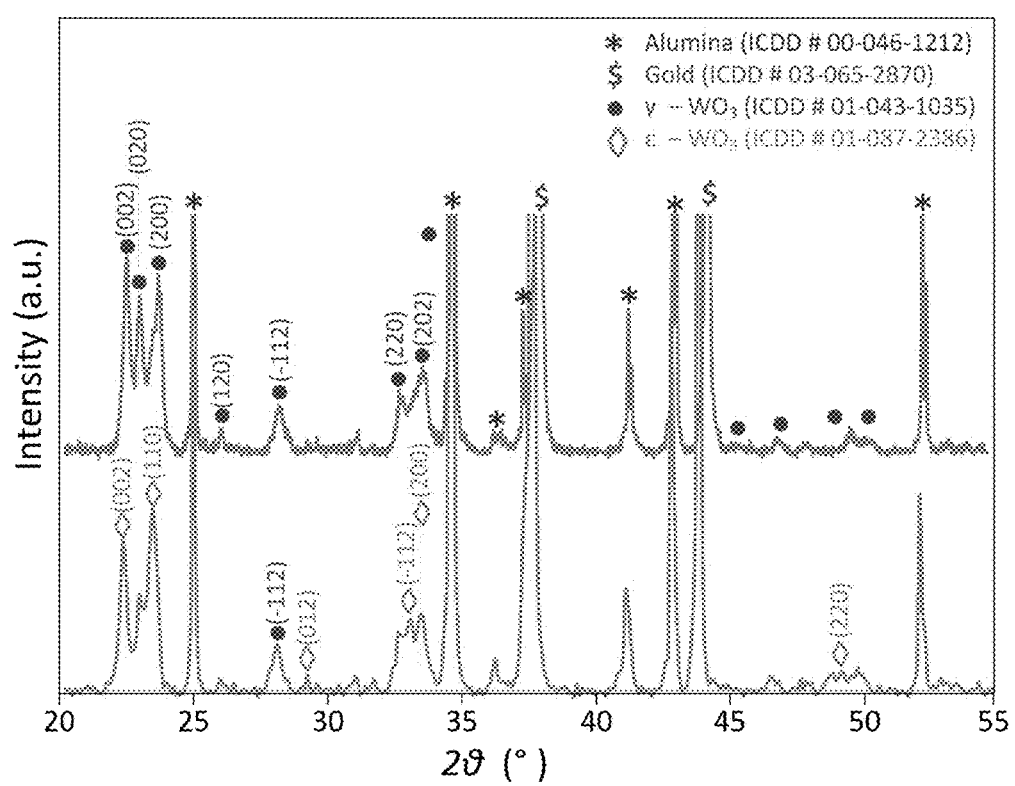
FIG. 21 shows X-ray diffraction of the $WO_3$ film before and after the acetone sensing stability test.

Results:

X-Ray Diffraction (XRD):

FIG. 21 shows the XRD pattern of the $WO_3$ film coated on gold interdigitated electrodes pre acetone test and after 450 h stability test. The characteristic peaks of ε-$WO_3$ (ICDD#01-087-2386), and γ-$WO_3$ (ICDD#01-043-1035) are shown. The characteristic main peaks for ε-$WO_3$ were seen at the 2θ value of 23.1°, 24.1°, 29°, 33.3°, 34°, and 49.4° and can be associated with the (002), (110), (012), (−112), (200) and (220) reflections, respectively.

Figure 22:
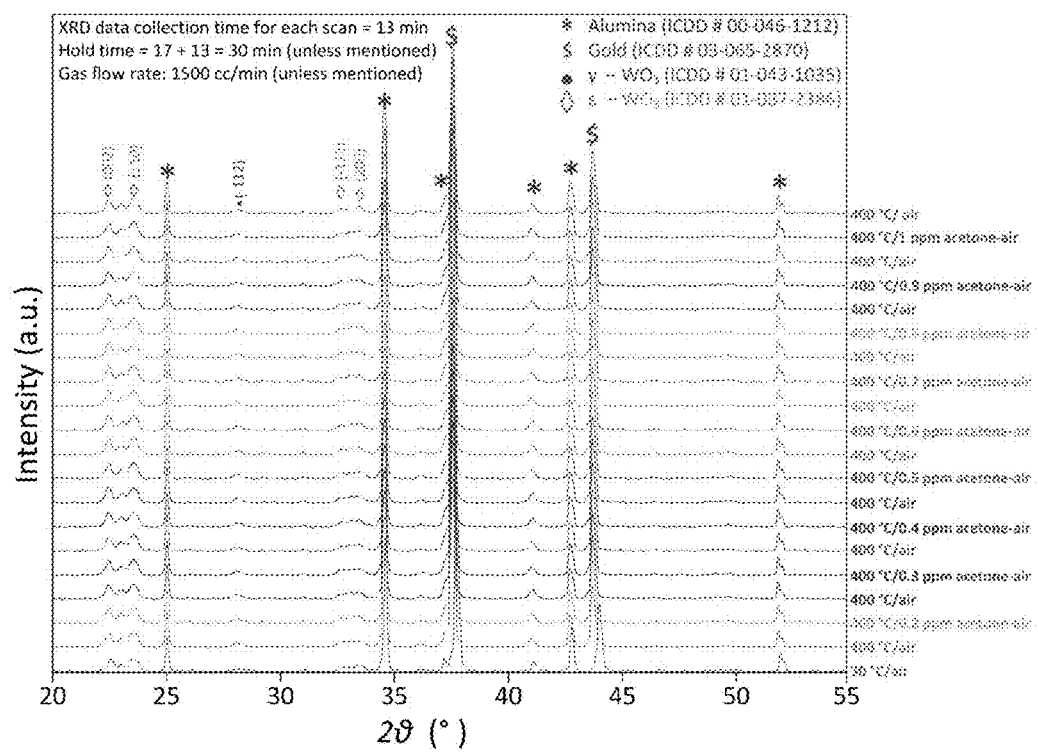
FIG. 22 shows Operando X-ray diffraction of the $WO_3$ film during 0.2 to 1 ppm acetone tests.

However, no change in the overall structure of the film was observed verifying that the film was stable under the acetone test conditions. FIG. 22 shows the XRD of sample at the conditions of the acetone test (operando XRD). It can be seen that the structure of the film has remained unchanged during the operando XRD confirming that the structure is stable during the acetone sensing experiments.

Figure 23:
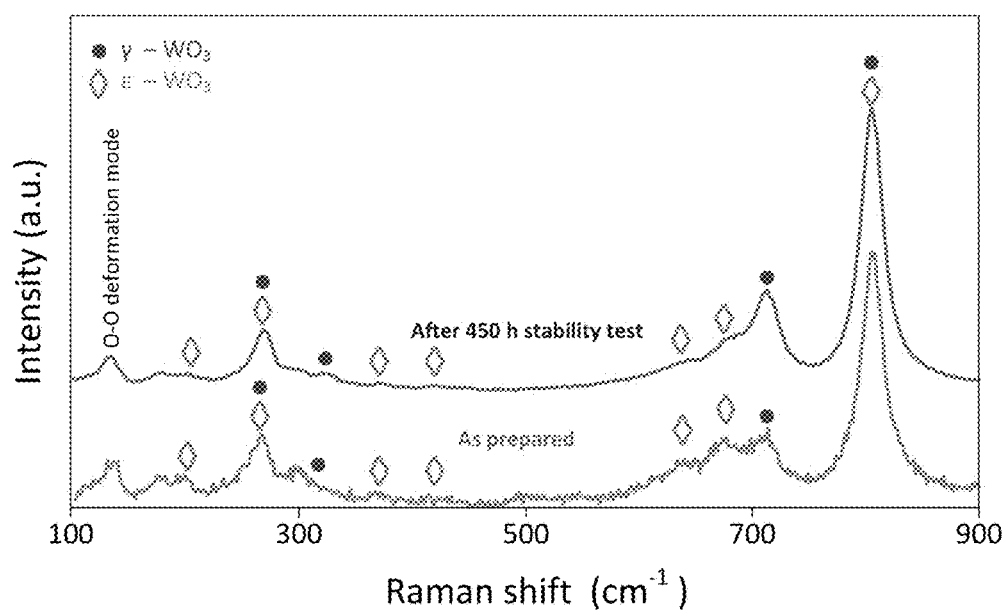
FIG. 23 shows Raman spectroscopy of the $WO_3$ film before and after the acetone sensing stability test.
Figure 25:
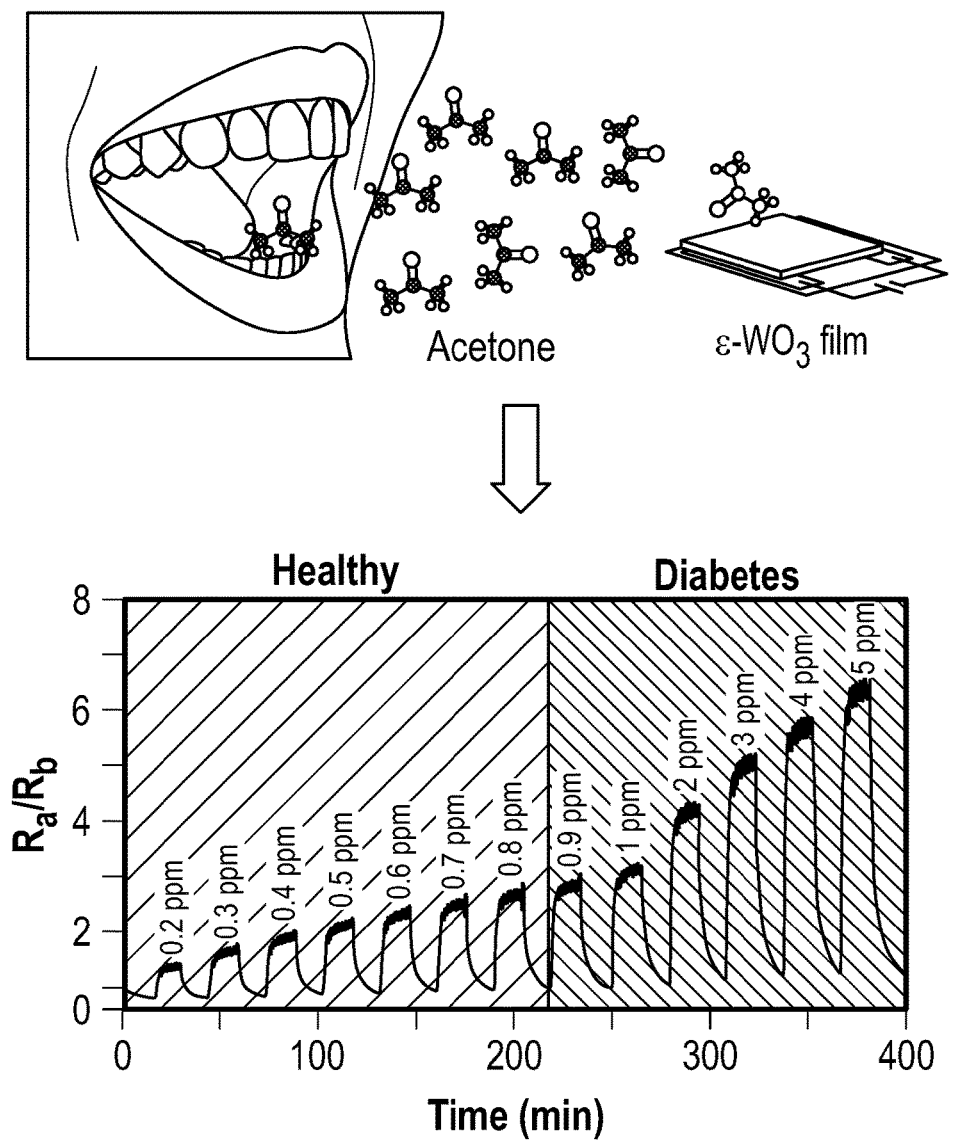
FIG. 25 is a schematic showing ultra-low acetone detection by an exemplary sensor assembly of the present disclosure (e.g., a sensor assembly having an epsilon $WO_3$ film on a substrate that was synthesized by Reactive Spray Deposition Technology).

Raman Spectroscopy:

Raman spectroscopy technique was used for identifying the phases in the $WO_3$ film since this technique is well known to give the "fingerprint" of $WO_3$ material. FIG. 23 shows the Raman spectroscopy results of the $WO_3$ film directly deposited on gold interdigitated electrodes, both pre and post acetone stability tests. The peaks were matched with the standards in references. The peaks for γ-$WO_3$ are at the Raman shift value of 808, 716, 328 and 275 cm$^{-1}$ while the peaks for ε-$WO_3$ are at 808, 686, 646, 423, 373, 275 and 208 cm$^{-1}$.

A relatively strong peak was observed below 150 cm$^{-1}$ for all the samples which indicates the O—O deformation mode. The strong γ-$WO_3$ peak at 715 cm$^{-1}$ is weak in the as prepared sample while the characteristic ε-$WO_3$ only peaks at 686, 646, 423, 373 cm$^{-1}$ are stronger. On the basis of XRD and Raman spectroscopy results, it can be concluded that the structure of the $WO_3$ film in this study is monoclinic c phase. Phase transformation from ε to γ is also evident after 450 hours of stability tests.

Electron Microscopy:

Scanning Electron Microscopy:

FIGS. 24A-24D show the SEM micrographs of the $WO_3$ film as deposited on the gold electrode. FIGS. 24A and 24C show the image after 8.5 hours acetone tests and it can be inferred from the images that the $WO_3$ film surface is rough and porous with the formation of some agglomerates around 5 to 10 μm wide.

Various pores can be seen which is advantageous for the diffusion of gases in the bulk of the film. FIGS. 24B and 24D show the image after 300 hours acetone tests. It can be clearly seen that there is a remarkable change in the morphology of the films after acetone stability tests. From FIGS. 24A and 24B, uniformly coated gold lines with $WO_3$ can be seen and it can be inferred that the film formation is conformal in nature. The total $WO_3$ deposition area on the gold electrodes was 97.5 mm$^2$. The images indicate high quality porous $WO_3$ films deposited by RSDT without any cracks, voids, dense regions or surface abnormalities.

Transmission Electron Microscopy:

FIG. 4 shows the bright field TEM micrograph of the $WO_3$ particles. Necking of the grains can be clearly observed which is advantageous for the enhanced electron transport through the percolation path (grain to grain contact) as described by researchers. Various oval shaped particles can be seen. From TEM point analysis, a crystallite size ($d_{TEM}$) distribution ranging between 12 to 25 nm was observed.

It has been shown that the gas sensitivity is significantly enhanced when the crystallite size is smaller than the Debye length ($\Lambda_D$). This is because both the surface and bulk of the grain contributes to the resistance and yields the largest gas sensor response. The Debye length for $WO_3$ is 25 nm. No evidence of sintering of the nanoparticles was found which is attributed to the use of air quench in RSDT.

Gas Sensing Results:

FIG. 5 shows the resistance versus time curve for the acetone concentration ranging from 0.2 to 1 ppm in the air at 400° C. The limit of detection for the tests was 0.2 ppm. The film resistance decreases as the concentration of acetone is increased. This is because of the increased adsorption of acetone molecules at higher acetone concentration. The adsorption and desorption of the acetone molecules on the $WO_3$ film takes place simultaneously and is a reversible process.

During the response stage, adsorption is higher than desorption and the resistance of the film increases. This is because acetone diffuses through the porous $WO_3$ film and reduces the $WO_3$ surface thereby depleting the ionosorbed oxygen concentration on the film. Acetone also captures electrons from the conduction band of $WO_3$ causing the formation of an electron depletion region, triggering an increase in its resistance. It was seen that the sensor response was spontaneous as the gas concentration in the test chamber was changed from pure air to acetone in the air. The response time was calculated to be 10 seconds. The sensor very quickly stabilized at the maximum value of resistance.

At this point, the adsorption rate is equal to the desorption rate. Maximum adsorption had taken place at that particular analyte concentration, and the $WO_3$ film was in equilibrium with the acetone molecules. Recovery of the sensor started when pure air was switched back to the test chamber. At this point, adsorption was nil and desorption was the only process which was taking place. Presence of two vents in the test chamber expedited the exchange of the gas atmosphere. However, it was seen that desorption was still slower than adsorption. A drift can be seen when the resistance of the film is measured in air after exposure to acetone at different concentrations. This is caused by incomplete recovery during the 15 minutes of recovery phase.

Stability Tests:

Stability tests of the $WO_3$ films were conducted for 450 hours at 0.5 ppm acetone in the air at 400° C. and which is same as the breath acetone concentration of a healthy individual. The sensor was tested at this concentration because it is desirable that the breath acetone concentration remain below the diabetes threshold limit.

0.5 ppm acetone was switched on every 5 minutes (response) followed by 5 minutes of pure air (recovery). Resistance of the film was measured every 100 ms to record the response and recovery cycle (response+recovery time=10 min).

A total of 2700 response-recovery cycles were recorded. FIG. 6 shows the resistance over time for $WO_3$ film in pure air ($R_a$) and 0.5 ppm acetone in air ($R_g$), respectively. It can be seen that the sensor is stable till day 10 (around 250 hours). From day 10 to 21 (250-450 hours) the sensor began to degrade possibly due to the growth of the $WO_3$ nanoparticles and the phase transformation to the γ phase as confirmed by XRD and Raman spectroscopy. This shows that maximum degradation of the sensor occurred after day 10 (around 250 hours) as evident from the fluctuation of resistance.

Selectivity:

The response of 0.5 ppm acetone was compared with 10 ppm $H_2$, 0.2 ppm ethanol, 8 ppm CO and 90% relative humidity in air at 400° C. It was seen that the sensor had negligible response for ethanol, CO and humidity, but significant response for 10 ppm $H_2$. $H_2$ is a major component exhaled from the human breath. Typical values of $H_2$ in the breath range from 10 to 20 ppm.

Discussion:

On the basis of the characterization and gas sensing results, one can conclude that RSDT can be used for the synthesis of acetone sensing films directly on gold interdigitated electrodes. Based on work on $WO_3$ and a review of literature, it can be shown that some of the characteristics of the sensing device that are important for good performance are: (1) high porosity of the sensing film, (2) particle size of the sensing film smaller than the Debye length ($\lambda_D$), a characteristic of the semiconductor material, which is 25 nm for $WO_3$, (3) film thickness, (4) absence of impurities in the test atmosphere, (5) test chamber volume, and (6) time required for the exchange of gases in the test chamber. In this Example, the importance of these factors are identified and it is shown that the gas sensing test data presented in this Example adheres to these requirements.

Since the sensing is an adsorption-desorption process, gas diffusion through the film plays a major role in the sensor performance. The sensing film should be porous to effectively allow the diffusion process and extend the reaction between acetone and oxygen from the surface to the bulk. By assuming steady state conditions, it can be interpreted that the acetone concentration decreases with the film depth which causes the formation of various degree of reactions at different depths of the film. The resistance change data recorded by the electrochemical analyzer averages the resistances by providing the overall resistance change of the film. It would be beneficial to eliminate this variation. Film porosity, thickness, microstructure, and the electrode pattern are some factors which govern this variation.

From the SEM micrographs in FIGS. 24A-24D, it can be seen that the $WO_3$ film synthesized by RSDT is highly porous and uniform. For porous layers, the active surface area is much larger than the dense layers. Two different transport mechanism for the charge carriers have been proposed for the porous layers:

Diffusion Theory:

According to the diffusion theory in porous layers, the conductance is calculated by the following equation:

$$C_{diff} = \text{area} * \left(\frac{q^2 n_b \mu_b}{k_B T}\right) * \sqrt{\frac{q n_b V_z}{2\varepsilon}} * \exp\left(\frac{-q v_s}{k_B T}\right) \quad \text{(Equation 1)}$$

Where "C" is the conductance and "area" has the dimensions in $m^2$ and represents the active area seen by the electrons while travelling from grain to grain. The subscript "b" represents bulk. The other symbols are as defined previously.

Thermoelectronic Emission Theory:

According to this theory, only the electrons which possess the kinetic energy greater than the band bending height can move across the boundary. The net current is the difference in the charge fluxes across the boundary from left to right and right to left respectively.

$$C_{thermo} = \text{area} * \left(\frac{q}{k_B T}\right) * q * \sqrt{\frac{\varepsilon * k_B * T}{\pi * m'}} * \exp\left(\frac{-q v_s}{k_B T}\right) \quad \text{(Equation 2)}$$

Where, $\sqrt{\dfrac{\varepsilon * k_B * T}{\pi * m'}}$ = mean thermal velocity of the carriers and $m'$ is the effective mass. The other symbols are as defined previously.

Gas sensing response is dependent on the particle size of the sensing film. Smaller particles and increased surface area (higher surface to volume ratio) provides larger number of sites for the surface reaction to occur. At the same time, reducing the particle radius below $\Lambda$, will converge the electron depletion layer ($2\Lambda$), and the electrical conduction will be dominated by the presence of adsorbed acetone species. $\Lambda$ depends on the Debye length ($\lambda_D$) of the material by the following equation:

Debye length by the following equation:

$$\Lambda = \lambda_D \left( \dfrac{2qV_s}{k_B T} \right)^{1/2} \quad \text{(Equation 3)}$$

$qV_s$ = height of band bending, $\lambda_D$ = Debye length $k_B$ = Boltzmann's constant = $1.38 * 10^{-23} \dfrac{J}{K'}$, $T$ = temperature Debye length of $WO_3$ is 25 nm. Researchers have described the relationship between gas sensitivity and particle size with respect to the Debye length ($\lambda_D$). When the particle size is smaller than $\lambda_D$, the ionosorbed oxygen will extract all the electrons from the $WO_3$ particle causing an increase in film resistance. In this Example, the $WO_3$ particle size were in the range 12 to 25 nm as determined by the TEM point analysis.

Selectivity is a concern for a sensor to be commercially viable, which may lead to false alarm or incorrect gas concentration determination. In this Example, it was found that the $WO_3$ film was responsive to 10 ppm $H_2$, while the response to humidity, 0.2 ppm ethanol and 8 ppm CO was negligible.

There are various methods to discriminate the interference to these gases that are suggested in the literature. A common approach is to utilize a sensor array with various sensor electrodes to filter out the response from the interfering analytes. Another method is to use filters upstream of the electrode to filter out the gases. One such activated charcoal filter is used by Figaro Inc. in their commercial CO sensor—TGS5042.

Since the sensor response is a diffusion driven process, filters can be applied to improve the selectivity. Porous layers in which gases may have different diffusion coefficients can be directly deposited on the sensing layer. These layers acts as molecular sieves to reject the interfering gases. Description of these porous layer filters have been provided. Pre-calibration of the sensor for known cross contaminants has also been suggested.

The long recovery time and the drift of the metal oxides based sensors have been long recognized and various suggestions to counter this limitation have been proposed. From the gas sensing tests in FIG. 6, a drift can be seen when the resistance of the film is measured in air after exposure to acetone at different concentrations. This is caused because of incomplete recovery during the 15 minutes of recovery phase.

As a gas molecule is chemically adsorbed on the surface of $WO_3$, it is in thermal equilibrium and resides at the bottom of the potential well (minimum potential energy). In order to desorb from the surface, the only driving force it experiences is the diffusion caused by the change in the concentration of gases in the test chamber on switching to pure air. However, this energy is not sufficient and causes a long delay to achieve complete desorption. Further thermal or electrical energy is required to expedite this adsorption process. Different ways are suggested in literature to eliminate sensor drift. These include, using high-speed gas-switching system and smaller volume test chamber for enabling quicker gas exchange, pre exposing the sensing film to the analyte for a set period of time, use of mathematical function and modeling to pre-estimate the steady state conditions and remove the time lag, use of multiple sensing electrodes in different test chamber to alter between response and recovery, use of neural network algorithm for the sensor to "self-learn," use of strong negative field to electro-desorb the residual analyte molecules to "refresh" the sensor and by illuminating the sensor with ultra-violet (UV) light. Here a two vent test chamber was used to expedite the atmosphere change. The test chamber volume was 85 cc. A prototype sensing device can be developed with a volume of 0.5 cc which will further reduce this issue.

CONCLUSIONS

In this Example, RSDT has been evaluated as a direct deposition technique for the synthesis of $\varepsilon$-$WO_3$ film for ultra-low acetone sensing. Air quenching was used to optimize the particle size and film morphology to tailor the film towards superior acetone sensing performance.

A main objective was to correlate the influence of the synthesis process, and the resultant structural properties of the $\varepsilon$-$WO_3$ film with the acetone gas sensing performance. These properties have been highlighted, and their influence on the acetone sensing which will provide a platform for developing better sensors with improved performance compared to the currently used sensors. Some reasons for the high response can be attributed to a number of factors, such particle size, porosity and pore size, and film thickness, all precisely controlled by the RSDT.

At least the following conclusions can be made from this Example:

1) RSDT synthesized $WO_3$ film based acetone sensor was responsive in the 0.2 to 1 ppm range, when tested at 400° C.

2) XRD and Raman spectroscopy confirmed the presence of $\varepsilon$-$WO_3$.

3) Operando XRD at the same conditions of acetone tests confirmed that the structure was unaltered during the tests.

4) Response time was 10 seconds and recovery time was greater than 15 minutes.

5) The acetone sensors gave a steady response till 450 hours of continuous performance and started to degrade after 450 hours possibly due to phase transformation to the thermodynamically stable $\gamma$-$WO_3$.

6) Interference was negligible with humidity, 0.2 ppm ethanol, and 8 ppm CO; however, it was significant with 10 ppm $H_2$.

7) Response and recovery of the sensor can be caused by adsorption and desorption, respectively. Hence recovery time can be improved by expediting the desorption step.

8) $WO_3$ particle size of less than 25 nm attributes to better charge transfer which translates to superior acetone sensitivity.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. A sensor assembly comprising:
a substrate;
a dopant-free metal oxide film deposited on the substrate, the dopant-free metal oxide film having amorphous phase boundaries around the outer edges of particles of the dopant-free metal oxide film;
wherein the dopant-free metal oxide film is adapted to facilitate detection of an analyte in a sample;
wherein the dopant-free metal oxide film is porous and has a film thickness of from 500 nm to 3 microns; and
wherein the dopant-free metal oxide film is adapted to facilitate detection of 0.20 parts per million of the analyte in the sample in less than 10 seconds.

2. The assembly of claim 1, wherein the substrate includes gold or platinum inter-digitated electrodes.

3. The assembly of claim 1, wherein the substrate is a micro-electro-mechanical-system substrate having a set of inter-digitated electrodes.

4. The assembly of claim 1, wherein the dopant-free metal oxide film includes gamma $WO_3$ or epsilon $WO_3$.

5. The assembly of claim 1, wherein the dopant-free metal oxide film is selected from the group consisting of a $WO_3$, $TiO_2$, ZnO, $CeO_2$, $WO_x$ and $CeO_x$ film.

6. The assembly of claim 1, wherein the dopant-free metal oxide film includes amorphous phase boundaries around the outer edges of nanoparticles of the dopant-free metal oxide film.

7. The assembly of claim 6, wherein the nanoparticles have a size from 2 nm to about 10 nm.

8. The assembly of claim 1, wherein the dopant-free metal oxide film includes metal oxide phases that are stable at room temperature.

9. The assembly of claim 1, wherein the dopant-free metal oxide film has uniform necking between particles of the dopant-free metal oxide film.

10. The assembly of claim 1, wherein the dopant-free metal oxide film is adapted to facilitate detection of the analyte for 450 hours of continuous testing of the sample at a working temperature of from 250° C. to 400° C.

11. The assembly of claim 1, wherein the analyte is a gas and the sample includes exhaled breath.

12. The assembly of claim 1, wherein the analyte is acetone and the sample includes exhaled breath.

13. The assembly of claim 1, wherein the analyte is $NO_2$ or $NO_x$.

14. The assembly of claim 1, wherein the analyte is a component of exhaled breath that correlates with a health condition.

15. The assembly of claim 1, wherein the analyte is selected from the group consisting of acetone, $NO_2$, $NO_x$, isoprene, $CO_2$, CO, $O_2$, ethanol and $H_2$.

16. A sensor assembly comprising:
a substrate, the substrate a micro-electro-mechanical-system substrate having a set of gold or platinum inter-digitated electrodes;
a dopant-free metal oxide film deposited on the substrate, the dopant-free metal oxide film having amorphous phase boundaries around the outer edges of nanoparticles of the dopant-free metal oxide film, the nanoparticles having a size from 2 nm to 10 nm;
wherein the dopant-free metal oxide film includes gamma $WO_3$ or epsilon $WO_3$;
wherein the dopant-free metal oxide film is porous and has a film thickness of from 500 nm to 3 microns;
wherein the dopant-free metal oxide film has uniform necking between nanoparticles of the dopant-free metal oxide film;
wherein the dopant-free metal oxide film is adapted to facilitate detection of an analyte in a sample;
wherein the analyte is a component of exhaled breath that correlates with a health condition;
wherein the dopant-free metal oxide film is adapted to facilitate detection of the analyte for 450 hours of continuous testing of the sample at a working temperature of from 250° C. to 400° C.; and
wherein the dopant-free metal oxide film is adapted to facilitate detection of 0.20 parts per million of the analyte in the sample in less than 10 seconds.

* * * * *